US012678259B2

(12) United States Patent
Scheller et al.

(10) Patent No.: US 12,678,259 B2
(45) Date of Patent: Jul. 14, 2026

(54) SURGICAL ILLUMINATION SYSTEM

(71) Applicant: Katalyst Surgical, LLC, Chesterfield, MO (US)

(72) Inventors: Steven Scheller, Chesterfield, MO (US); Eric J. Bass, St. Louis, MO (US); Anthony Kiel, Troy, MO (US); Gregg D. Scheller, Wildwood, MO (US); Carl C. Awh, Nashville, TN (US)

(73) Assignee: Katalyst Surgical, LLC, Chesterfield, MO (US)

( * ) Notice: Subject to any disclaimer, the term of this patent is extended or adjusted under 35 U.S.C. 154(b) by 332 days.

(21) Appl. No.: 18/181,891

(22) Filed: Mar. 10, 2023

(65) Prior Publication Data

US 2023/0285108 A1     Sep. 14, 2023

Related U.S. Application Data

(60) Provisional application No. 63/318,743, filed on Mar. 10, 2022.

(51) Int. Cl.
| *A61B 90/30* | (2016.01) |
| *A61F 9/007* | (2006.01) |
| *F21V 8/00* | (2006.01) |
| A61B 17/00 | (2006.01) |

(52) U.S. Cl.
CPC .............. *A61B 90/30* (2016.02); *A61F 9/007* (2013.01); *G02B 6/0006* (2013.01); *A61B 2017/0023* (2013.01); *A61B 2017/00345* (2013.01); *A61B 2017/00526* (2013.01); *A61B 2090/306* (2016.02)

(58) Field of Classification Search
CPC ......................... A61B 90/30; A61B 2090/306
See application file for complete search history.

(56) References Cited

U.S. PATENT DOCUMENTS

| 7,470,269 | B2 | 12/2008 | Auld et al. |
| 8,491,549 | B2 | 7/2013 | Conston et al. |
| 10,420,460 | B2 | 9/2019 | Scheller |
| 10,888,219 | B2 | 1/2021 | Smith et al. |
| 2006/0184162 | A1 | 8/2006 | Smith |

(Continued)

FOREIGN PATENT DOCUMENTS

| CA | 2 832 502 A1 | 11/2012 |

OTHER PUBLICATIONS

International Search Report and Written Opinion for corresponding Application No. PCT/US23/64111 dated Aug. 28, 2023 (14 pages).

(Continued)

*Primary Examiner* — Julianna N Harvey
(74) *Attorney, Agent, or Firm* — NIXON PEABODY LLP; Jeffrey L. Costellia

(57) ABSTRACT

A surgical illumination system includes a light source having at least one laser diode configured to emit a light beam, the light beam having a focal point at a focal point plane, an optical fiber with a proximal portion configured to receive the light beam from the light source and a distal portion configured to emit the light beam from the light source, the proximal portion having an aperture opening. The size of the focal point is less than the size of the aperture opening.

15 Claims, 16 Drawing Sheets

(56)        References Cited

U.S. PATENT DOCUMENTS

| | | | |
|---|---|---|---|
| 2006/0270908 A1* | 11/2006 | Luloh | A61B 3/0008 600/182 |
| 2007/0191823 A1 | 8/2007 | Scheller | |
| 2008/0246919 A1 | 10/2008 | Smith | |
| 2012/0203075 A1* | 8/2012 | Horvath | A61B 90/30 600/249 |
| 2013/0128223 A1* | 5/2013 | Wood | A61B 3/1208 351/246 |
| 2015/0366443 A1 | 12/2015 | Liolios et al. | |
| 2016/0346058 A1 | 12/2016 | Bacher et al. | |
| 2017/0156581 A1 | 6/2017 | Smith et al. | |
| 2018/0062344 A1* | 3/2018 | Smith | G01J 1/4257 |
| 2018/0214238 A1 | 8/2018 | Dos Santos et al. | |
| 2018/0344153 A1 | 12/2018 | Svetliza et al. | |
| 2019/0046288 A1 | 2/2019 | Anderson et al. | |
| 2019/0094564 A1 | 3/2019 | Rivera et al. | |
| 2019/0239979 A1 | 8/2019 | Abt | |
| 2019/0269556 A1 | 9/2019 | Meckel et al. | |
| 2019/0314111 A1 | 10/2019 | Lassalas et al. | |
| 2020/0022773 A1 | 1/2020 | Grueebler et al. | |
| 2020/0278486 A1 | 9/2020 | Svetliza et al. | |
| 2021/0007824 A1 | 1/2021 | Timoszky et al. | |
| 2021/0011274 A1 | 1/2021 | Otterstrom et al. | |
| 2022/0409325 A1 | 12/2022 | Kiel et al. | |

OTHER PUBLICATIONS

International Search Report and Written Opinion for corresponding Application No. PCT/US2023074019 dated Mar. 26, 2024 (23 pages).
International Preliminary Report on Patentability for PCT Application No. PCT/US2023/074019, dated Sep. 18, 2025, (17 pages).
Jan. 21, 2026 Extended European Search Report issued in corresponding European Patent Application No. 23767732.3, 10 pp.

* cited by examiner

SURGICAL ILLUMINATION SYSTEM

CROSS REFERENCE TO RELATED APPLICATIONS

This application claims priority to U.S. Application No. 63/318,743 filed 10 Mar. 2022, the subject matter of which is herein incorporated by reference in its entirety.

BACKGROUND OF THE INVENTION

The subject matter herein relates generally to a surgical illumination system, and in particular an ophthalmic illumination system with a light beam having a focal point modulated to an opening aperture of an optical fiber to provide illumination to a surgical site during a surgical procedure.

Various ophthalmic surgical procedures, sometimes referred to as vitreo-retinal procedures, are commonly performed in the posterior segment of the eye. Ophthalmic surgical procedures are appropriate to treat many serious conditions of the posterior segment, such as age-related macular degeneration (AMD), diabetic retinopathy and diabetic vitreous hemorrhage, macular hole, retinal detachment, epiretinal membrane, CMV retinitis, and many other ophthalmic conditions.

During the surgical procedures, proper illumination of the inside of the eye is important. Typically, ophthalmic illumination systems, such as endoilluminator systems include a light source and a fiberoptically illuminated microsurgical device to provide light to the surgical site. A user, such as a surgeon or other medical professional, can insert the microsurgical device into the eye to illuminate the inside of the eye. The light source and other illumination optics direct a light beam into an optical fiber of the illuminated microsurgical device.

It is desirable to minimize the number and size of incisions required to perform ophthalmic surgical procedures. Typically, incisions are only made large enough to accommodate the size of the microsurgical instrument being inserted into the interior of the eye. Therefore, minimizing the size of the microsurgical instrument can minimize the incision size and eliminate the need to surgical sutures. Reducing the number of incisions may be accomplished by integrating various microsurgical instruments. For example, the optical fiber may be incorporated into the working end of a microsurgical instrument to eliminate the need for a separate illumination incision.

However, prior attempts at integrating multiple microsurgical instruments resulted in larger instruments requiring larger incisions or were accompanied by a corresponding decrease in the performance of one or all of the integrated surgical instruments. For example, the size of the optical fiber used in microsurgical instruments has been limited by the size and volume of the light beam emitted by conventional light sources that use conventional light elements, such as Tungsten, Halogen, incandescent, Metal Halide arc, Xenon arc, Mercury Vapor arc, and LED.

All of the LED, incandescent, and arc sources within these lamps are large relative to the size of the fibers that they are coupled with. Generally, conventional light sources are limited to use with optical fibers with a diameter of 200 microns or greater. These conventional light sources are not capable of emitting a light beam with a focal point that is smaller than an opening aperture of the optical fiber. As a result, reducing the size of the optical fiber would reduce the amount of light transmitted by the optical fiber to an unacceptable level of performance.

Accordingly, there is a need for an surgical illumination system having a light source that can emit a light beam with a focal point modulated to an opening aperture of an optical fiber for illuminating a surgical site during a surgical procedure.

BRIEF DESCRIPTION OF THE INVENTION

In one embodiment, a surgical illumination system is provided and includes a light source having at least one laser diode configured to emit a light beam. The light beam has a focal point at a focal point plane. The surgical illumination system includes an illumination microsurgical device removably coupled to the light source. The illumination microsurgical device includes an optical fiber with a proximal portion configured to receive the light beam from the light source and a distal portion configured to emit the light beam from the light source. The proximal portion has an aperture opening. The size of the focal point is less than the size of the aperture opening.

In another embodiment, an illumination microsurgical device is provided and includes an optical fiber having a proximal portion configured to receive a light beam from a laser diode of a light source and a distal portion configured to emit the light beam. The proximal portion includes an aperture opening which has a diameter of less than 200 microns. The illumination microsurgical device includes a device connector at the distal portion. The device connector is configured to be removably coupled to the light source. The illumination microsurgical device includes a surgical tool configured to be inserted into the patient. The distal end of the optical fiber is integrated into the surgical tool for insertion of the distal end of the optical fiber into the patient. The optical fiber, the device connector, and the surgical tool are disposable after use.

In a further embodiment, a method of manufacturing a surgical illumination system is provided. The method provides a light source having at least one laser diode configured to emit a light beam. The method couples an illumination microsurgical device to the light source to receive the light beam. The illumination microsurgical device includes an optical fiber transmitting the light beam from a proximal portion to a distal portion. The proximal portion has an aperture opening. The method focuses the light beam at a focal point at a focal point plane. The size of the focal point is less than the size of the aperture opening.

DETAILED DESCRIPTION OF THE INVENTION

Figures 1, 2:
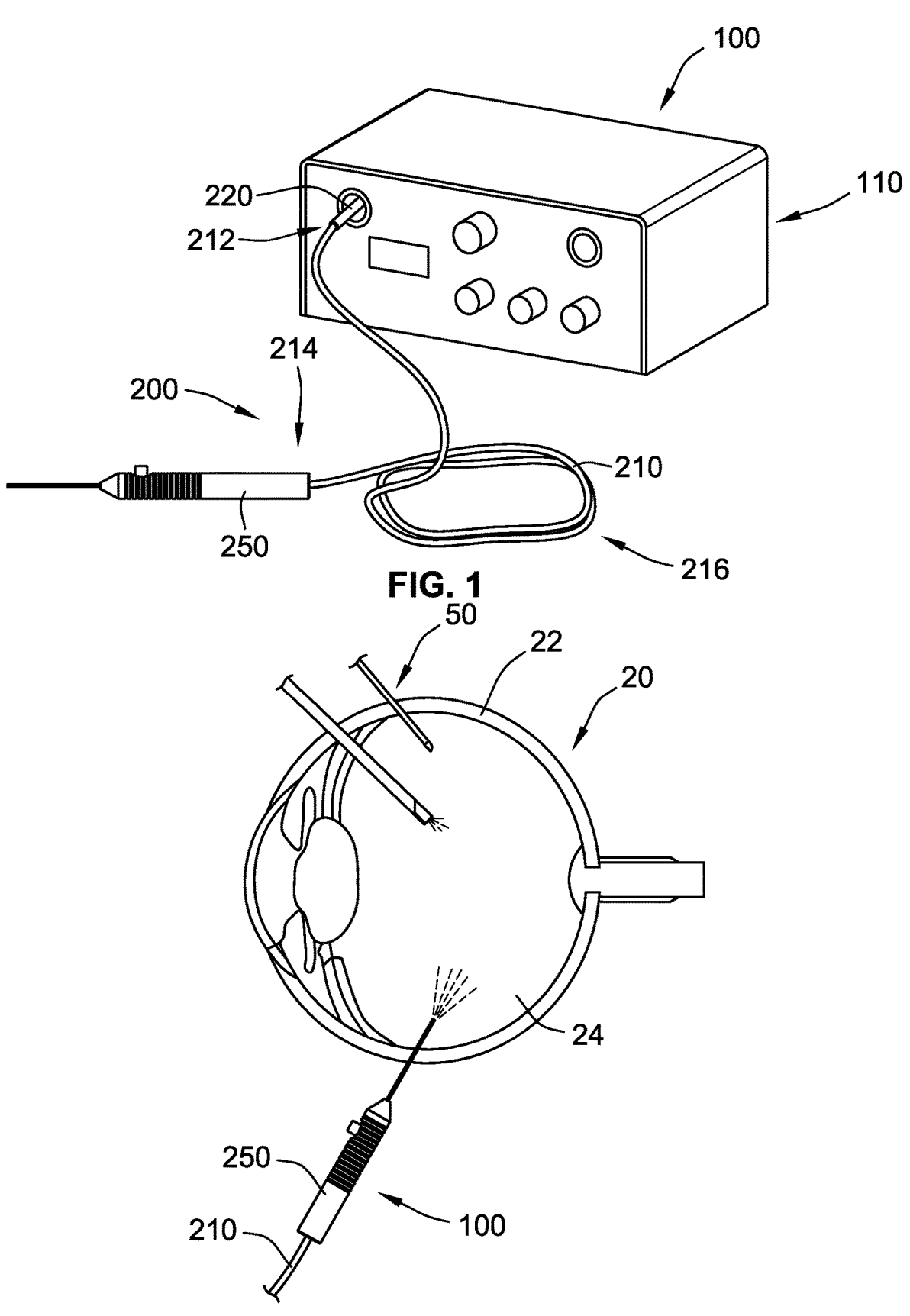
FIG. 1 illustrates a surgical illumination system in accordance with an exemplary embodiment.
FIG. 2 is a cross-section view of the surgical illumination system illuminating an interior region of an eye in accordance with an embodiment.

FIG. 1 illustrates a surgical illumination system 100 in accordance with an exemplary embodiment. The surgical illumination system 100 is used to provide illumination to a surgical site during a surgical procedure. In various embodiments, the surgical illumination system 100 is an ophthalmic illumination system used for imaging an eye during an ophthalmic surgical procedure, such as vitreo-retinal procedures. The surgical illumination system 100 may be used to treat ophthalmic conditions of the posterior segment of the eye, such as age-related macular degeneration (AMD), diabetic retinopathy and diabetic vitreous hemorrhage, macular hole, retinal detachment, epiretinal membrane, CMV retinitis, and many other ophthalmic conditions. The surgical illumination system 100 may be used for other surgical procedures in alternative embodiments performed on other parts of the patients body.

The surgical illumination system 100 includes a light source 110 and an illumination microsurgical device 200 for performing a surgical procedure. The light source 110 is used to illuminate the illumination microsurgical device 200 and/or the patient through the illumination microsurgical device 200. The light source 110 generates a light beam. The illumination microsurgical device 200 receives the light beam and transmits the light beam through an optical fiber 210 to illuminate a surgical field. The illumination microsurgical device 200 includes a surgical tool 250 for performing use in the surgical procedure and a device connector 220 for connecting the illumination microsurgical device 200 to the light source 110. The device connector 220 may be removably coupled to the light source 110, such as to dispose of the illumination microsurgical device 200 after use and replace with a new illumination microsurgical device 200. The optical fiber 210 may be integrated with the surgical tool 250. The surgical tool 250 may be a lighting tool, a cutting tool, an aspiration tool, an irrigation tool, a forcep tool, or another type of tool for aiding the physician in performing the surgical procedure.

The optical fiber 210 has a proximal portion 212, a distal portion 214, and a central portion 216 extending between the proximal portion 212 and the distal portion 214. The optical fiber 210 is configured to receive the light beam at the proximal portion 212. The optical fiber 210 is configured to output the light beam from the distal portion 214. The distal portion 214 is provided at the surgical tool 250. For example, the distal portion 214 may pass through the surgical tool 250. The distal portion 214 may be embedded in the surgical tool 250. The distal portion 214 may extend from the end of the surgical tool 250. The distal portion 214 may be movable relative to the surgical tool 250, such as to change the lighting pattern. In an exemplary embodiment, the optical fiber 210 is configured to emit the light beam from the light source 110 to the surgical field in an expanded light pattern relative to the originally emitted light pattern from the light source 110. The light beam output may be at a high intensity, such as greater than 10 Lumen. In various embodiments, the light output beam may be greater than 20 Lumen, such as 30 Lumen or more. The color temperature of the light output may be adjustable. In various embodiments, the color temperature may be between 5500-6000K, however the color temperature may be adjustable up to 8300K in various embodiments. In an exemplary embodiment, the optical fiber 210 has a very small diameter, allowing use of smaller surgical tools 250 and/or allowing smaller incisions or openings in the patient to perform the invasive surgical procedure. In various embodiments, the optical fiber 210 may be sized with a diameter of less than 200 microns. The optical fiber 210 may be sized with a diameter in the range of about 50 microns to 100 microns. In an exemplary embodiment, the light source 110 utilizes one or more laser diodes to generate the light beam having sufficient lighting for the very small diameter optical fiber 210.

FIG. 2 is a cross-section view of the surgical illumination system 100 illuminating an interior region of an eye 20 in accordance with an embodiment. The surgical tool 250 may be inserted through a sclera 22 (generally at the pars plana) into a vitreous region 24 in connection with performing a vitreo-retinal procedure. The eye 20 may be illuminated by the optical fiber 210 through the surgical tool 250. Various other microsurgical instruments 50 may additionally be inserted into the eye 20 during various intra-operative procedures, such as vitreo-retinal surgery. For example, the microsurgical instruments may include, but are not limited to, a vitrectomy probe, an infusion cannula, cutting probe, an aspiration probe, scissors, forceps, or other types of microsurgical probes.

Figure 3:
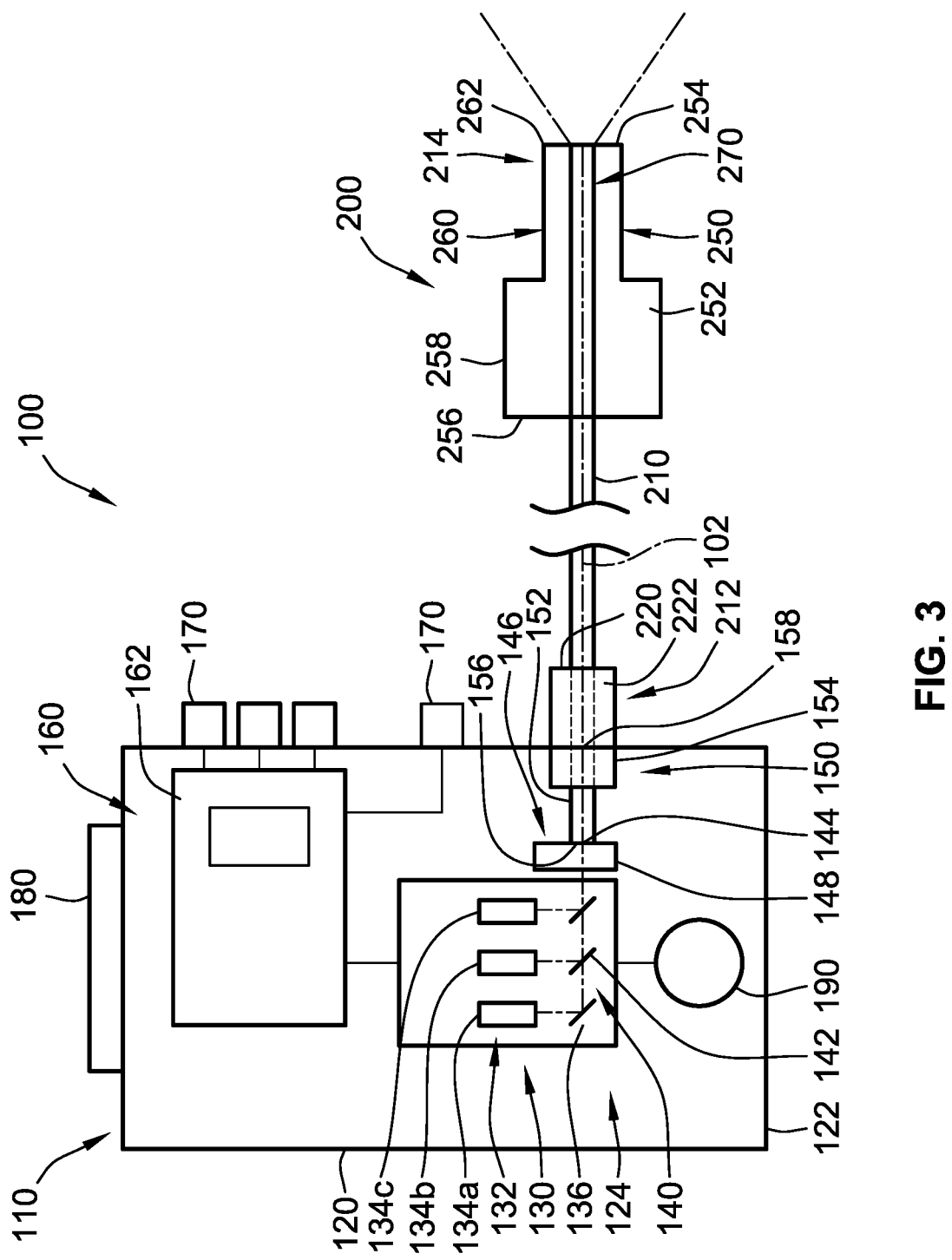
FIG. 3 is a schematic diagram of the surgical illumination system in accordance with an exemplary embodiment.

FIG. 3 is a schematic diagram of the surgical illumination system 100 in accordance with an exemplary embodiment. The surgical illumination system 100 includes the light source 110 and the illumination microsurgical device 200 connected to the light source 110. The illumination microsurgical device 200 receives the light beam 102 from the light source 110.

The illumination microsurgical device 200 includes the optical fiber 210, the surgical tool 250 for performing use in the surgical procedure and the device connector 220 for connecting the illumination microsurgical device 200 to the light source 110. For example, the surgical tool 250 is provided at the distal portion 214 for insertion into the patient and the device connector 220 is provided at the proximal portion 212 for removable connection to the light source 110. The optical fiber 210 is configured to emit the light beam 102 from the light source 110 to the surgical field in an expanded light pattern relative to the originally emitted light pattern from the light source 110. In an exemplary embodiment, the optical fiber 210 has a very small diameter, allowing use of smaller surgical tools 250 and/or allowing smaller incisions or openings in the patient to perform the invasive surgical procedure.

The light source 110 includes a light source housing 120 having walls 122 forming an internal cavity 124. The light source 110 includes a light assembly 130 received in the cavity 124. The light assembly 130 generates a light beam 102. In an exemplary embodiment, the light source 110 includes a bridge assembly 150 between the light assembly 130 and the illumination microsurgical device 200. The bridge assembly 150 receives the light beam 102 and transmits the light beam 102 from the light assembly 130 to the illumination microsurgical device 200. The light source 110 includes a controller 160 for controlling the light assembly 130. The light source 110 includes one or more user inputs 170, operably coupled to the controller 160, for the physician to control the light assembly 130. Optionally, the light source 110 may include a display 180 for displaying information to the physician, such as one or more operating parameters (for example, brightness, color, or other characteristics of the light beam 102). In various embodiments, the light source 110 includes a vibratory despeckling mechanism 190.

The light assembly 130 includes one or more light elements 132 for generating the light beam 102. The light assembly 130 can output a diagnostic light beam, a treatment light beam, and/or an illumination light beam. The light beam 102 can include any suitable wavelength(s) of light, such as visible light, infrared light, ultraviolet (UV) light, etc. For example, the light beam 102 can transmit bright, broadband, and/or white light to illuminate a surgical field when employed during the surgical procedure.

In an exemplary embodiment, the light elements 132 are laser diodes 134. The laser diodes 134 generate different color light beams, such as light beams at different wavelengths. The outputs from the laser diodes 134 are combined to form the light beam 102. The laser diodes 134 may be operated independently to control the characteristics of the light beam 102. When employing laser diodes, the emitted light beam 102 generally possesses a high degree of spatial coherence. High spatial coherence typically enables the beam to be focused to small spot sizes for delivery to fiber optic cabling. The ability to focus light emitted from the laser diodes 134 to small spot sizes may enable the use of small-scale optical fibers for transmitting the light to the interior of eye. Small-scale optical fibers generally have a diameter (or other largest cross-sectional dimension) of less than 200 microns. In various embodiments, the optical fibers may have diameters of 100 microns or less, such as 50 microns. The size of the focused beam may have a spot size of less than the diameter of the optical fiber for efficient transmission to the optical fiber, and thus enhanced brightness from the optical fiber. When integrated with microsurgical instruments, the small diameter of the small scale optical fiber may enable a reduction in the cross-sectional area of the instrument, which in turn may reduce the size of the surgical incision in the sclera of the eye through which the instrument is inserted.

In an exemplary embodiment, the light source 110 includes an array of three laser diodes 134 that are arranged to combine and emit a single light beam that can be modulated to produce a predetermined spectral range. The laser diodes 134 generate highly collimated output beams. The color temperature of the output beams are adjustable, such as by controlling the power to the laser diodes 134. Each of the laser diodes 134 may include a discrete spectral range, such as a generally blue spectral range, a generally green spectral range, and a generally red spectral range. In one embodiment, the generally blue spectral range may include a wavelength of about 440 nm to about 460 nm, the generally green spectral range may include a wavelength of about 510 nm to about 530 nm, and the generally red spectral range may include a wavelength of about 650 nm to about 670 nm. The generally blue spectral range should have a wavelength that is within a safe region of the aphakic hazard level. Although the embodiment includes three laser diodes 134, greater or fewer laser diodes 134 may be used. In the illustrated embodiment, the three laser diodes 134 include a red laser diode 134a, a green laser diode 134b, and a blue laser diode 134c. The red laser diode 134a is configured to emit a red light beam in the red spectral range. The green laser diode 134b is configured to emit a green light beam in the green spectral range. The blue laser diode 134c is configured to emit a blue light beam in the blue spectral range. The laser diodes 134 are mounted to a circuit board 136 and operably coupled to the controller 160. Operation of the laser diodes 134 is controlled by the controller 160. For example, the controller 160 may independently control ON/OFF of the various laser diodes 134 and/or intensity/brightness of the laser diodes 134. The color may be adjusted during the surgery, such as to enhance parts, features, or issues of the patient's eye.

In an exemplary embodiment, the light assembly 130 includes a beam combiner 140 configured to combine the individual beams from the laser diodes 134 into the light beam 102. The beam combiner 140 includes lenses or mirrors 142 to focus the laser beams along a common path. For example, the mirrors may be hot or cold dichroic mirrors or fold mirrors. The light assembly 130 may include other components, such as a condenser having a plurality of lenses to focus the light beam 102 output by the laser diodes 134. The light assembly 130 may include beam splitters, lenses, gratings, filters, and/or combinations thereof, which facilitate the transmission of light to the optical fiber 210. The beam combiner 140 directs the laser beams to a focal point 144 at a focal point plane 146. The individual laser beams from the laser diodes 134 are focused and/or combined at the focal point 144. For example, the individual laser beams are directed along a common path passing through the focal point 144. In an exemplary embodiment, a lens assembly 148 is provided to focus the beam to the focal point 144 at the focal point plane 146. The bridge assembly 150 is provided at the focal point plane 146 to receive the light beam 102. The lens assembly 148 may include one or more lenses, filters or other focusing optics for transmitting the light beam 102 into a diffraction limited focused spot having an area (for example, diameter) that is less than the diameter of the component receiving the light beam (for example, the fiber optic), such as at the bridge assembly 150 and/or the optical fiber 210.

In an exemplary embodiment, the bridge assembly 150 includes a bridge optical fiber 152 and a light source connector 154. The bridge optical fiber 152 includes a first end 156 and a second end 158. The first end 156 is located at the focal point plane 146 to receive the light beam 102 from the light assembly 130. The light source connector 154 is provided at the second end 158. The illumination micro-surgical device 200 is coupled to the light source connector 154. The bridge assembly 150 transmits the light from the light assembly 130 to the illumination microsurgical device 200. The light source connector 154 may include a ferrule or other type of fiber optic connector to connect the bridge optical fiber 152 with the optical fiber 210 of the illumination microsurgical device 200. In an exemplary embodiment, the light source connector 154 defines a separable interface with the illumination microsurgical device 200 to allow removal of the illumination microsurgical device 200 from the light source 110, such as for disposal and replacement of the illumination microsurgical device 200. In an alternative embodiment, rather than using the bridge optical fiber 152, the light beam 102 may be transmitted from the light assembly 130, through air/free space, directly into the optical fiber 210 of the illumination microsurgical device 200. For example, the light source connector 154 may precisely position the optical fiber 210 to receive the light beam 102 from the light assembly 130.

The controller 160 includes a control circuit board 162 and one or more electrical components mounted to the control circuit board 162. The electrical components may include one or more processors, memories, drivers, and the like. The control circuit board 162 is connected to the user inputs 170 to receive inputs from the user inputs 170. The user inputs 170 may be buttons, dials, sliders, keypads, touchpads, or other types of user inputs. In various embodiments, a user input 170 may be provided for independent control of each of the laser diodes 134, such as to control the intensity/frequency of the laser diodes 134 independently. The user input 170 may include a brightness input to control brightness of the light beam 102. In various embodiments, the user inputs 170 can be independently adjusted by the user to modulate the spectral ranges of each laser diode 134. The user inputs 170 may include presets that allow the user to select a predetermined color or spectral range. The control circuit board 162 is connected to the display 180 to provide output to the display 180. The display 180 may include a visual indicator that displays the color and/or brightness of the selected spectral range of the final light beam emitted from the system 100, which may allows the user to preview the color or spectral range prior to use in a patients eye. The control circuit board 162 is connected to the light assembly 130, such as to the circuit board 136 of the light assembly 130 to control the laser diodes 134. For example, the control circuit board 162 may supply control signals or power to the laser diodes 134 to control operation of the laser diodes 134.

The vibratory despeckling mechanism 190 is operably coupled to the light assembly 130. For example, the vibratory despeckling mechanism 190 may be coupled to the circuit board 136 and/or the laser diodes 134 to vibrate the laser diodes 134 to reduce speckling in the light beam 102. In other various embodiments, the vibratory despeckling mechanism 190 may vibrate the bridge optical fiber 152 to reduce the speckling of the combined light beam and produce more uniform illumination. For example, the vibratory despeckling mechanism 190 may include a vibration element attached to a stripped optical fiber within the system. A light beam produced by combining multiple individual light beams to produce a single light beam having the spectral ranges of the individual light beams, such as implemented with light source 110, may be subject to a phenomenon referred to as speckling. Speckling occurs when multiple light waves having different phases interfere with one another. When added together, the interferences produce a light wave having an intensity that varies randomly. In alternate embodiments, options for reducing speckling include, for example, using rotating diffusers or lenses arranged in the optical path of the light beam to disrupt the spatial coherence of the emitted light beam.

The device connector 220 is configured to be removably coupled to the light source 110, such as to the housing 120 and/or the light source connector 154. The device connector 220 includes a connector housing 222. In an exemplary embodiment, the connector housing 222 includes a ferrule holding the end of the optical fiber 210. In various embodiments, the connector housing 222 may be threadably coupled to the hosing 120/light source connector 154. The connector housing 222 may include a threaded nut configured to be threadably coupled to the housing 120/light source connector 154.

The surgical tool 250 is provided at the distal end of the illumination microsurgical device 200. The surgical tool 250 includes a tool body 252 extending between an inner end 254 and an outer end 256. The inner end 254 is a working end configured to be inserted into the patient. The outer end 256 is a holding end configured to be held and manipulated by the physician to position the surgical tool 250 during the surgical procedure. In an exemplary embodiment, the surgical tool 250 includes a handle 258 at the outer end 256 configured to be held by the physician.

In an exemplary embodiment, the surgical tool 250 includes an operating portion 260 at the inner end 254. The operating portion 260 is configured to interact with the patient, such as to perform the surgical procedure. The operating portion 260 is configured to be inserted into the patient. In an exemplary embodiment, the operating portion 260 includes a probe 262 at the inner end 254 configured to be inserted into the patient. In various embodiments, the operating portion 260 includes a light pipe for illuminating the patient (for example, the eye) during the procedure. The light pipe may be a wide angle light pipe. The light pipe may be a narrow light pipe, such as a spot light. In various embodiments, the lighting may be variable, such as variable between narrow angle lighting and wide angle lighting to change the lighting during the procedure using the same surgical tool. In various embodiments, the operating portion 260 includes a surgical tip configured to perform a surgical procedure. For example, the surgical tip may include a scalpel, scissors, forceps, a needle, a cannula, an irrigation device, an aspiration device, a multi-flex tool, and the like.

In an exemplary embodiment, the surgical tool 250 includes a cavity 270 through the interior of the surgical tool 250. The cavity 270 may be open at the inner end 254 and the outer end 256. The cavity 270 may be a cylindrical bore along a central axis of the surgical tool 250. The cavity 270 may have other shapes, such as being stepped or cone shaped. The cavity 270 receives the optical fiber 210. For example, the optical fiber 210 passes through the cavity 270 to the inner end 254 to emit the light forward of the surgical tool 250. The cavity 270 may receive another component, such as a cannula or needle that supports or holds the optical fiber 210.

In various embodiments, the surgical tool 250 is a disposable light pipe. The small optical fiber allows the wall thicknesses of the surrounding stainless steel tube of the light pipe to be thicker, such as making 25 and 27 gauge light pipes stiffer.

In various embodiments, the surgical tool 250 is a tangential illuminator configured for use during ILM procedures. The surgical procedure is enhanced because the ILM has a corrugated appearance under tangential illumination.

In various embodiments, the surgical tool 250 is an adjustable field output illuminator configured to be used to perform macular work under focal illumination and to perform peripheral retina membrane peeling under wide-field illumination using the same surgical tool and simply adjusting the lighting pattern without changing instruments. The small format fiber, having sufficient illumination from the high power light beam generated by the laser diodes, allows for effective wide to narrow field illumination, such as to see vitreous across the eye.

In various embodiments, the surgical tool 250 is an aspirating endoilluminator. The small fiber occupies smaller area in the instrument compared to conventional fiber optics thus allowing aspiration of the shredded pieces of membranes and removed from the eye by vacuum. The gap created between the small fiber and the inside diameter of the tubing allows membrane evacuation.

In various embodiments, the surgical tool 250 is a slit output illuminator. The light pipe may be manufactured to have a slit pattern light output to see a better cross-section of the eye during vitreous surgery due to the near-point light source provided by the optical fiber.

In various embodiments, the surgical tool 250 is a chandelier illuminator. The small diameter of the optical fiber reduces the size of the probe for mounting the chandelier illuminator to the eye. For example, the probe may be manufactured to be less than 25 gauge, thus reducing the possibility of wound leakage and eliminating the need for suture at the insertion site. The micro incision needed to insert the small diameter probe will allow the chandelier illuminator to be removed and replaced in a different location at the surgeons will without risk of leakage.

In various embodiments, the surgical tool 250 is an irrigating chandelier. The small optical fiber size allows more area for irrigating flow. The small-fiber format provides minimal in-flow interruption.

In various embodiments, the surgical tool 250 is an illuminated cannulas. The optical fiber is fed to a cannula head with the illumination coming out of the bottom of a transparent cannula tube. Instruments inserted through the cannula would "follow" the instrument tip with light. In addition, the cannula head would glow, which would eliminate the need to turn on the room lights in order for the surgeon to find the cannula hole again.

In various embodiments, the surgical tool 250 is an illuminated laser probe including both the optical fiber for illumination as well as another laser fiber to perform surgery, such as to perform vitrectomy. Illumination is more than adequate, and the surgeon can use the laser to achieve hemostasis during surgery. In various embodiments, the surgical tool 250 is a single-fiber illuminated laser probe having the laser and illumination down the same fiber.

Figure 4:
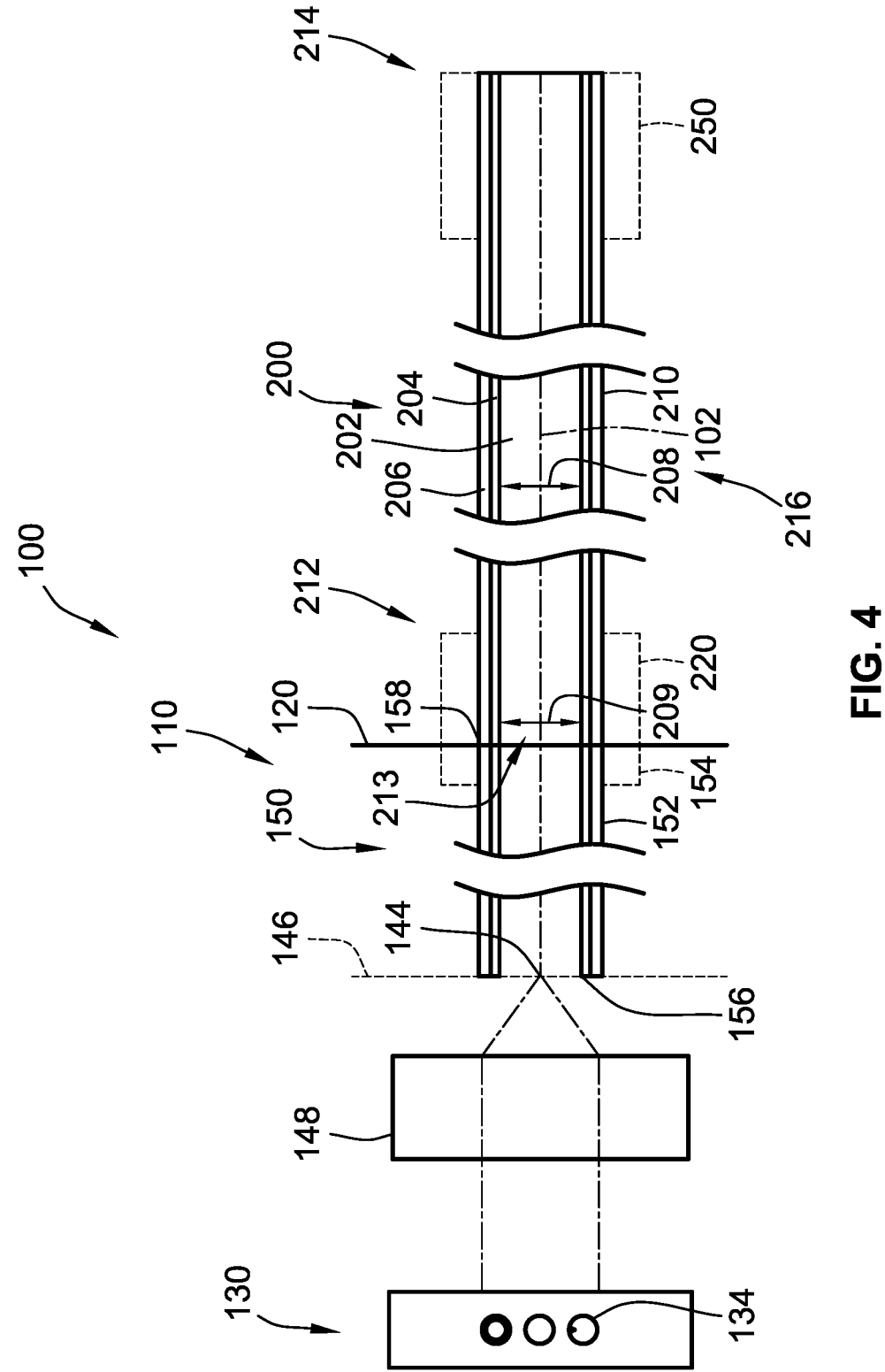
FIG. 4 is a diagram illustrating the surgical illumination system in accordance with an exemplary embodiment.

FIG. 4 is a diagram illustrating the surgical illumination system 100 in accordance with an exemplary embodiment. The surgical illumination system 100 includes the light source 110 and the illumination microsurgical device 200 connected to the light source 110. The illumination microsurgical device 200 includes the optical fiber 210, the surgical tool 250 for performing use in the surgical procedure and the device connector 220 for connecting the illumination microsurgical device 200 to the light source 110. The illumination microsurgical device 200 receives the light beam 102 from the light source 110 and emits the light beam 102 to the surgical field. The optical fiber 210 can have any suitable length. For example, the length can be between approximately 0.1 m and approximately 10 m. In an exemplary embodiment, the optical fiber 210 has a very small diameter, allowing use of smaller surgical tools 250 and/or allowing smaller incisions or openings in the patient to perform the invasive surgical procedure. The light source 110 of the surgical illumination system 100 includes at least one laser diode 134 configured to emit the light beam 102. The light beam 102 has the focal point 144 at the focal point plane 146. The optical fiber 210 receives the light beam 102 from the light source 110 and emits the light beam 102 from an end of the optical fiber 210. In an exemplary embodiment, the size of the focal point is less than the size of the aperture opening of the optical fiber 210.

The optical fiber 210 has the central portion 216 between the proximal portion 212 and the distal portion 214. The optical fiber 210 includes a core 202, a cladding 204 surrounding the core 202, and a coating 206 surrounding the cladding 204. The core 202 can be a cylinder of glass, plastic, silica, borosilicate, and/or other suitable material through which light propagates. The cladding 204 surrounds the core 202 and confines the light within the core 202. The cladding 204 includes a dielectric material with an index of refraction less than the index of refraction of the core 202. The coating 206 surrounds the cladding 204 and protects the optical fiber 210 from physical damage.

In an exemplary embodiment, the core 202 of the optical fiber 210 has a diameter 208. Optionally, the diameter 208 may be uniform/constant along the length of the optical fiber 210 (for example, along the proximal portion 212, the central portion 216, and the distal portion 214). In various embodiments, the proximal portion 212 may be cone shaped, such as widening from the central portion 216 to the proximal end of the proximal portion. In various embodiments, the distal portion 214 may be cone shaped, such as widening or narrowing from the central portion 216 to the distal end of the distal portion. In an exemplary embodiment, the core 202 of the optical fiber 210 has an inlet aperture opening 213 at the face of the proximal end 212. The inlet aperture opening 213 receives the light beam 102. The inlet aperture opening 213 has a diameter 209, which may be the same as the diameter 208 of the central portion 216 along the length of the optical fiber 210. The optical fiber 210 is configured to receive the light beam 102 through the inlet aperture opening 213 at the proximal portion 212. In an exemplary embodiment, the optical fiber 210 has a very small diameter, allowing use of smaller surgical tools 250 and/or allowing smaller incisions or openings in the patient to perform the invasive surgical procedure. In various embodiments, the diameter 208 and/or 209 of the optical fiber 210 may be sized with a diameter of less than 200 microns. The diameter 208 and/or 209 of the optical fiber 210 may be sized with a diameter in the range of about 50 micros to 100 microns. In an exemplary embodiment, spot size of the focal point of the laser diodes 134 of the light source 110 is less than the size of the inlet aperture opening 213. For example, the light source 110 and the optical fiber 210 have high optical efficiency. The light beam 102 is focused at the inlet aperture opening 213, such as by the lens assembly 148, to minimize or eliminate wasted or uncollected light. The laser diodes 134 are operated to generate the light beam having sufficient lighting for the very small diameter optical fiber 210.

In use, the light beam 102 traverses an optical path extending between the light source 110 and the surgical field, including through the optical fiber 210. The optical fiber 210 facilitates transmission of the light beam 102 between the light source 110 and the surgical tool 250. In various embodiments, the bridge assembly 150 is provided between the light assembly 130 and the optical fiber 210. For example, the bridge optical fiber 152 receives the light beam 102 from the light assembly 130 and emits the light beam 102 into the optical fiber 210. The first end 156 of the bridge optical fiber 152 is provided at the focal point plane 146 with the focal point 144 aligned with the first end 156 to direct the light beam 102 directly into the bridge optical fiber 152. In an exemplary embodiment, the bridge optical fiber 152 is an extension of the optical fiber 210. The bridge optical fiber 152 may be equivalent to the optical fiber 210, such as being manufactured form the same material and having the same diameter. The proximal portion 212 of the optical fiber 210 is optically coupled to the second end 158 of the bridge optical fiber 152. The proximal portion 212 may abut against the second end 158. The inlet aperture opening 213 receives the light beam 102 from the second end 158 of the bridge optical fiber 152. In alternative embodiments, the system may be provided without the bridge assembly 150. Rather, the light beam 102 may be emitted directly into the inlet aperture opening 213. For example, the inlet aperture opening 213 maybe provided at the focal point 144 at the focal point plane 146 rather than positioning the first end 156 of the bridge optical fiber 152 at the focal point 144 of the focal point plane 146.

The light source connector 154 positions and/or connects the bridge assembly 150 to the illumination microsurgical device 200. Optionally, the light source connector 154 may be directly coupled to the device connector 220 of the illumination microsurgical device 200. Alternatively, both the light source connector 154 and the device connector 220 of the illumination microsurgical device 200 may be connected to the housing 120. The light source connector 154 and/or the device connector 220 may include a ferrule or other type of fiber optic connector to connect the bridge optical fiber 152 with the optical fiber 210. In an exemplary embodiment, the illumination microsurgical device 200 includes a separable interface to allow removal of the illumination microsurgical device 200 from the light source 110, such as for disposal and replacement of the illumination microsurgical device 200.

Figure 5:
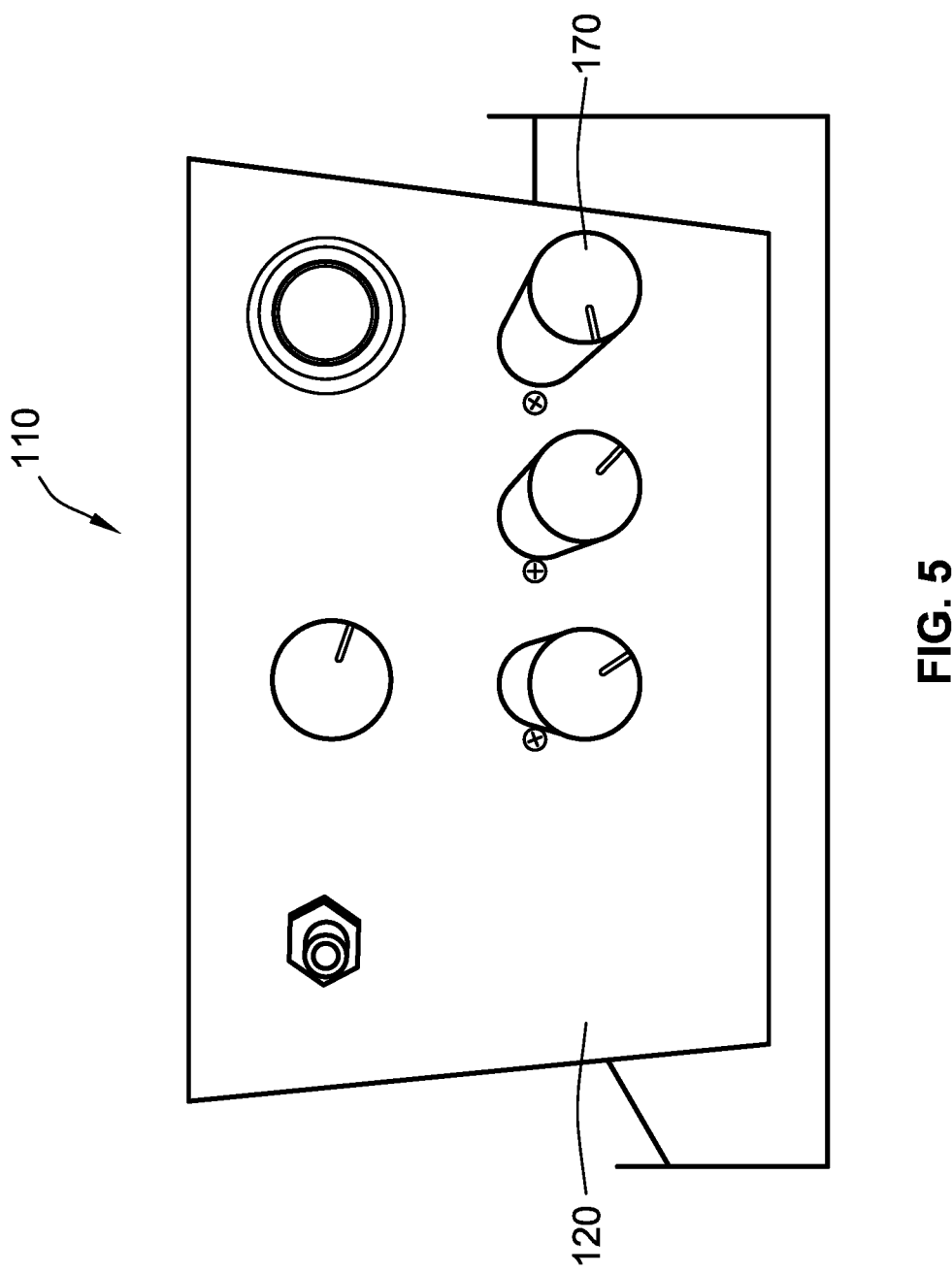
FIG. 5 is a front view of the light source in accordance with an exemplary embodiment.

FIG. 5 is a front view of the light source 110 in accordance with an exemplary embodiment. The light source 110 includes the light source housing 120. The light source 110 includes one or more user inputs 170, operably coupled to the controller 160, for the physician to control the light assembly 130. In the illustrated embodiment, the user inputs 170 are dials. However, other types of user inputs 170 may be used in alternative embodiments. In an exemplary embodiment, the user inputs 170 are configured to control the red laser diode, the green laser diode, and the blue laser diode to control the color of the combined light beam. The user inputs 170 may control the intensity or brightness of the light beams emitted by each of the laser diodes independently from one another and thereby controlling the color or color temperature of the combined the light beam.

Figure 6:
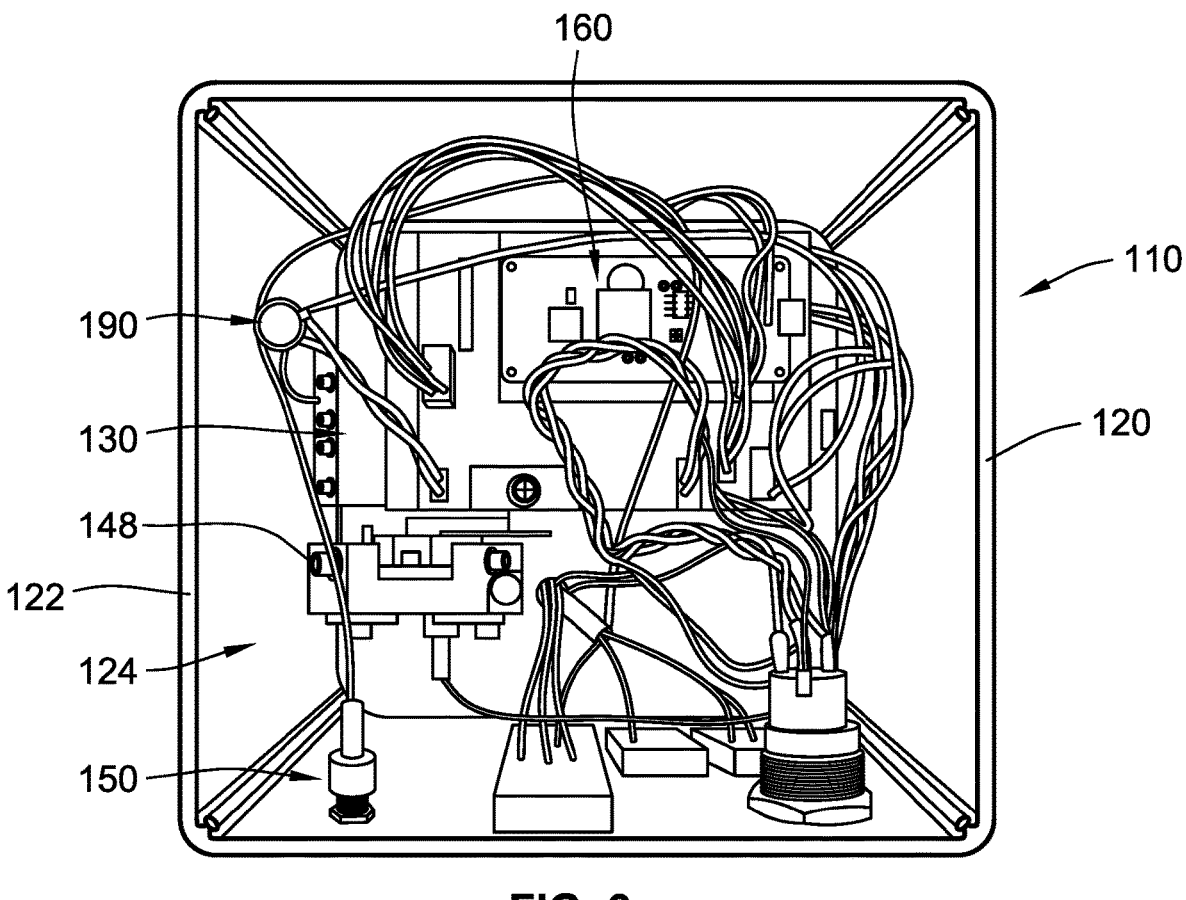
FIG. 6 is a top view of the light source with the cover removed to illustrate components of the light source in accordance with an exemplary embodiment.

FIG. 6 is a top view of the light source 110 with the cover removed to illustrate components of the light source 110 in accordance with an exemplary embodiment. The light source 110 includes the light source housing 120 having the walls 122 forming the internal cavity 124. The light source 110 includes the light assembly 130, the lens assembly 148, the bridge assembly 150, the controller 160, and the vibratory despeckling mechanism 190 for generating the light beam. Wires may be used to electrically connect the various components. The light assembly 130 directs the light beam at the focal point on the focal point plane, such as at the lens assembly 148. The bridge assembly 150 receives the light beam at the focal point plane and then directs the light beam to the optical fiber 210. However, in alternative embodiments, the lens assembly 148 may direct the light beam, through free space or air directly to the optical fiber.

Figure 7:
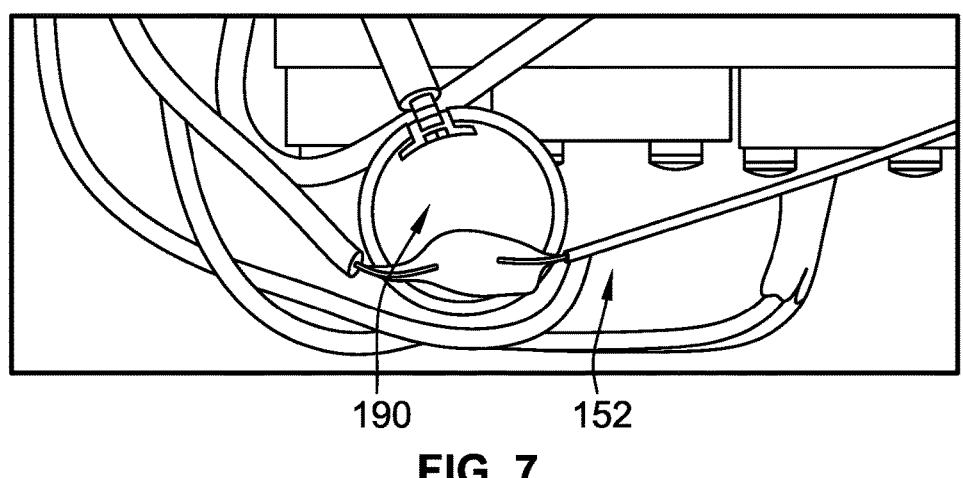
FIG. 7 is an enlarged view of a portion of the light source showing the vibratory despeckling mechanism in accordance with an exemplary embodiment.

FIG. 7 is an enlarged view of a portion of the light source 110 showing the vibratory despeckling mechanism 190 in accordance with an exemplary embodiment. An optical fiber, such as the bridge optical fiber 152, is connected to and vibrated by the vibratory despeckling mechanism 190 to reduce speckling of the combined light beam and produce more uniform illumination.

Figure 8:
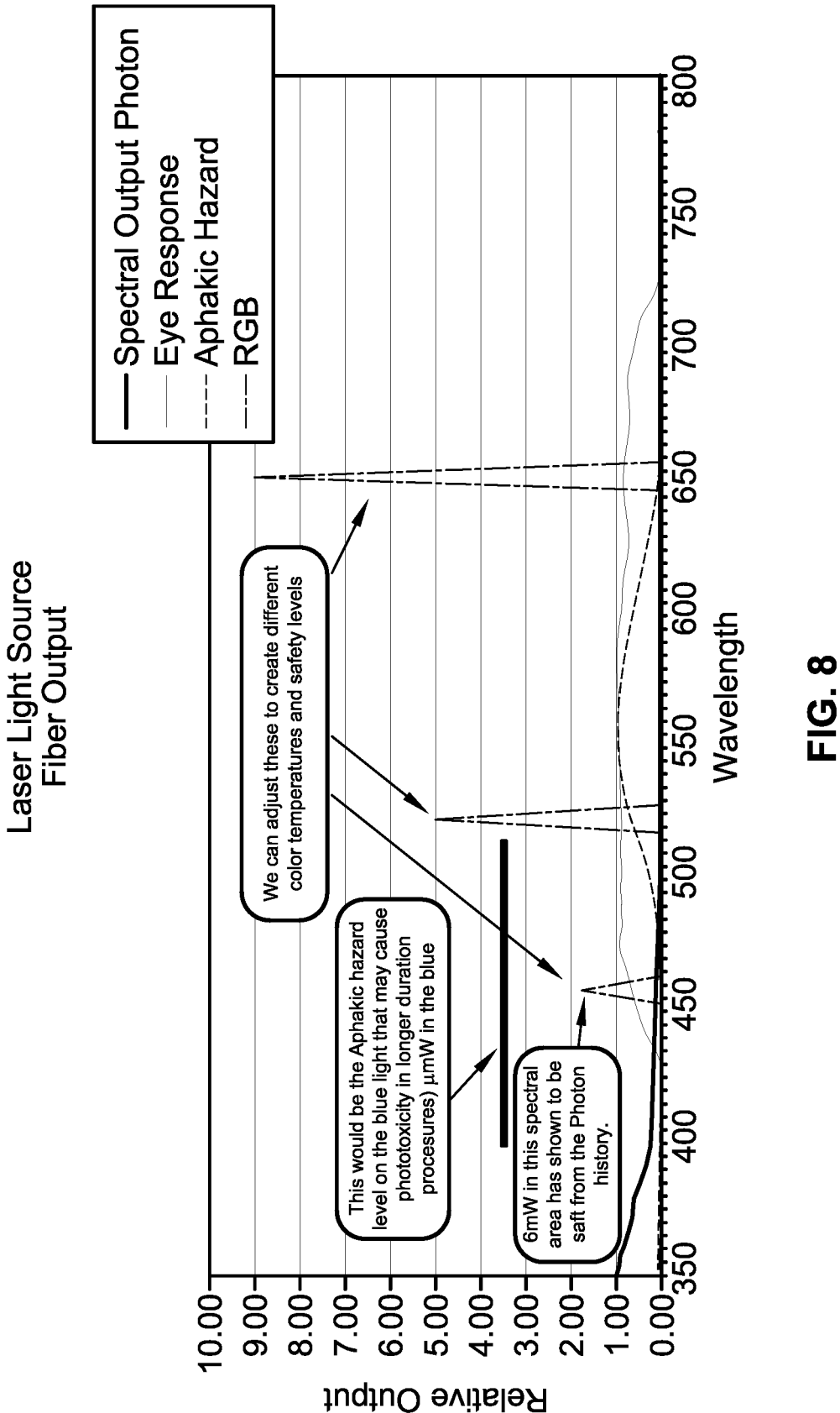
FIG. 8 is a graph showing output of the surgical illumination system in accordance with an exemplary embodiment.

FIG. 8 is a graph showing output of the surgical illumination system 100 in accordance with an exemplary embodiment. The light beam output from the light assembly to the optical fiber is combined from the multiple laser diodes (for example, red/green/blue) and can be modulated to produce a predetermined spectral range. Each of the laser diodes may emit in a discrete spectral range, such as a generally blue spectral range, a generally green spectral range, and a generally red spectral range. In one embodiment, the generally blue spectral range may include a wavelength of about 440 nm to about 460 nm, the generally green spectral range may include a wavelength of about 510 nm to about 530 nm, and the generally red spectral range may include a wavelength of about 650 nm to about 670 nm. The generally blue spectral range should have a wavelength that is within a safe region of the aphakic hazard level.

Generally, FIGS. 9-17 illustrate various embodiments of illuminated microsurgical instruments that may be used in conjunction with the surgical illumination system 100.

Figure 9A:
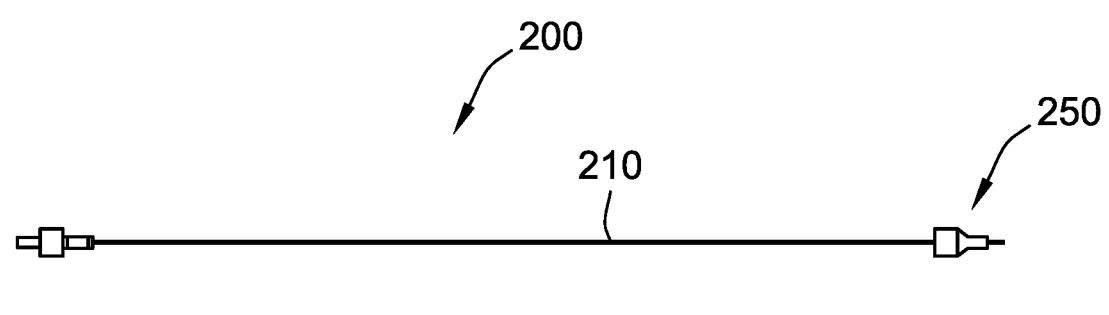
FIG. 9A is an overhead view of a first alternate embodiment of the illuminated microsurgical instrument.
Figure 9B:
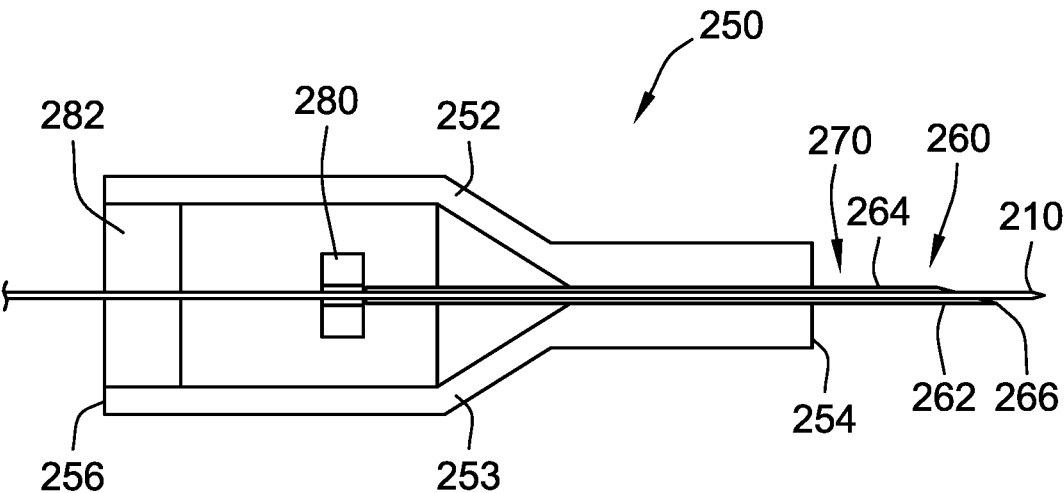
FIG. 9B is an enlarged cross-section view of the first alternate embodiment of the illuminated microsurgical instrument in an open position.
Figure 9C:
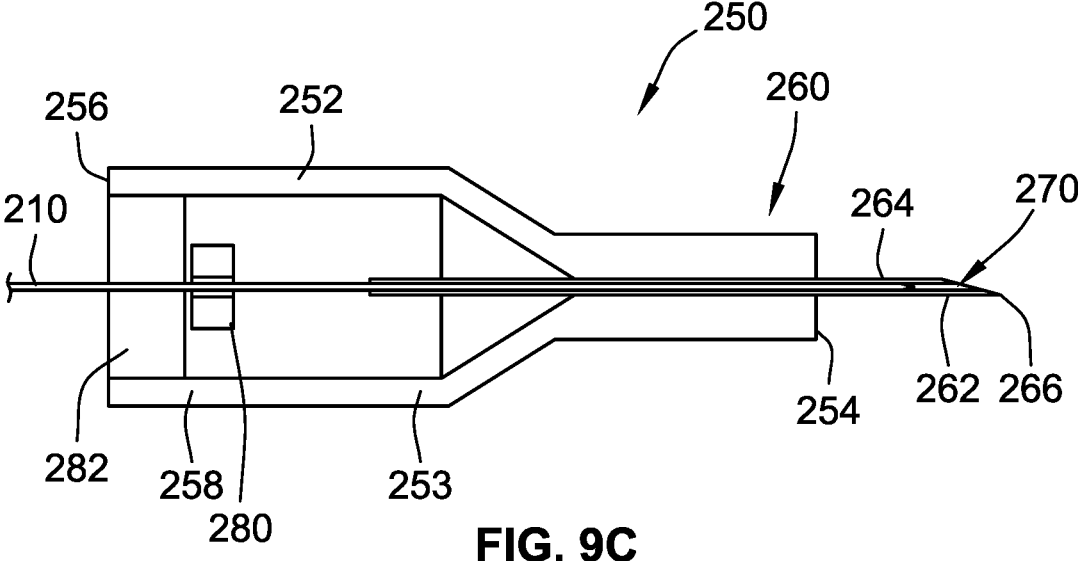
FIG. 9C is an enlarged cross-section view of the first alternate embodiment of the illuminated microsurgical instrument in a closed position.

FIG. 9A is an overhead view of an illumination micro-surgical device 200 in accordance with an exemplary embodiment. FIG. 9B is an enlarged cross-section view of a portion of the illumination microsurgical device 200 showing the surgical tool 250 and optical fiber 210 in accordance with an exemplary embodiment in an open position. FIG. 9C is an enlarged cross-section view of a portion of the illumination microsurgical device 200 showing the surgical tool 250 and optical fiber 210 in accordance with an exemplary embodiment in a closed position.

In the illustrated embodiment shown in FIGS. 9A-9C, the surgical tool 250 is a micro-chandelier. The micro-chandelier provides wide angle illumination of the interior of the eye during surgery. The small diameter of the optical fiber 210 and the high intensity and brightness of the light beam emitted from the optical fiber 210 make the surgical tool efficient for surgical procedures. The micro-chandelier is small enough to not need any suturing when removing from the eye. This allows the surgeon to easily move the chandelier to any location needed during surgery.

The surgical tool 250 includes the tool body 252 extending between the inner end 254 and the outer end 256. The surgical tool 250 includes the handle 258 at the outer end 256 configured to be held by the physician to load the operating portion 260 at the inner end 254 into the eye. For example, the probe 262 is provided at the inner end 254 for insertion into the eye.

In an exemplary embodiment, the surgical tool 250 includes the cannula or needle 264 received in the cavity 270. The optical fiber 210 passes through the needle 264. The needle 264 extends from the front end of a hub 253 of the tool body 252. The hub 253 is sized to be held with the finger or with a pair of needle holders/blunt forceps to position the surgical tool 250. The needle 264 has a tip 266. The needle 264 of the surgical tool 250 is beveled and sharp at the tip 266 to pierce the sclera as well as act as a shield to block glare. The optical fiber 210 is fixed inside of the hub 253 via a fiber stop 280 and a plug 282 on the back-side of the hub 254. The fiber stop 280 facilitates adjustability of the tip of the optical fiber 210 with respect to the tip 266 of the needle 264. The fiber stop 280 provides a limit to the adjustability by contact with the backside of the needle 264 and the plug 282 in the hub 253. The surgical tool 250 is inserted into the eye first by recessing the optical fiber 210 into the needle 264 until the fiber stop 280 is contacting the plug 282. The needle 264 is then inserted into the eye into the position the surgeon desires via his fingers or a pair of needle holders. The optical fiber 210 is then adjusted to the position desired by the surgeon. If the surgeon wishes to move the surgical tool 250 during the case, the optical fiber 210 may be recessed into the needle 264 and then the needle 264 may be removed from the eye. The surgeon is then able to re-insert the surgical tool 250 wherever they chose to.

Figures 10A, 10B, 10C, 10D:
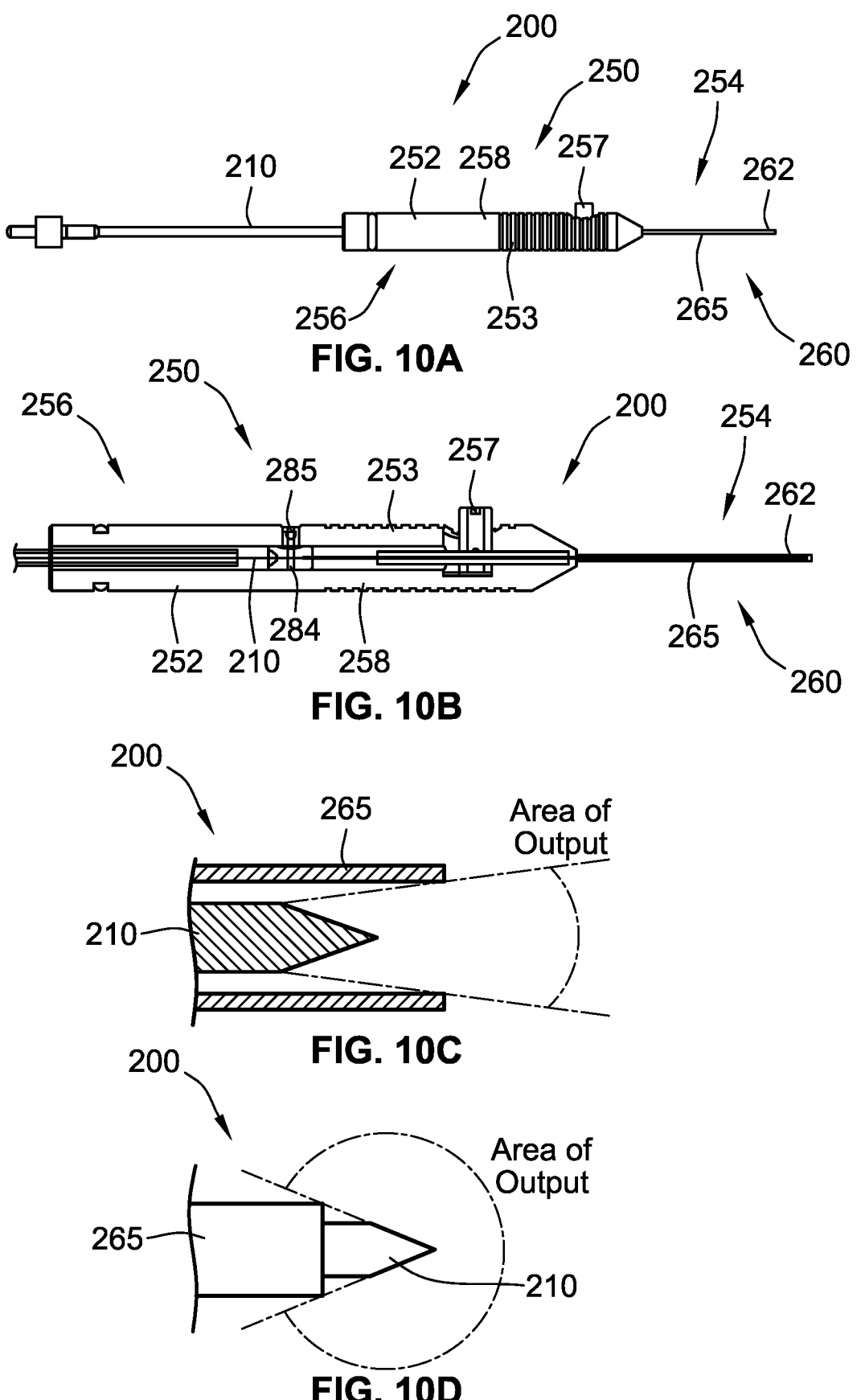
FIG. 10A is an overhead view of a second alternate embodiment of the illuminated microsurgical instrument.
FIG. 10B is cross-section view of a second alternate embodiment of the illuminated microsurgical instrument in a closed position.
FIG. 10C is an enlarged view of a second alternate embodiment of the illuminated microsurgical instrument with a non-beveled tip in a closed position.
FIG. 10D is an enlarged view of a second alternate embodiment of the illuminated microsurgical instrument with a non-beveled tip in an open position.
Figure 10E:
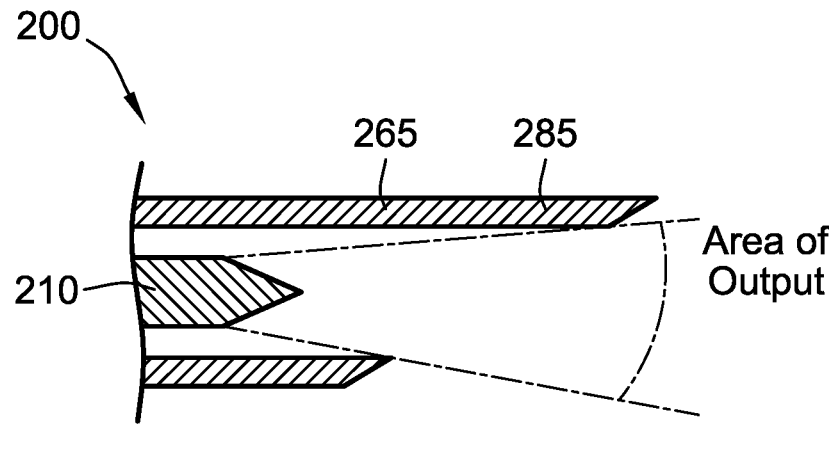
FIG. 10E is an enlarged view of a second alternate embodiment of the illuminated microsurgical instrument with a beveled tip in a closed position.
Figure 10F:
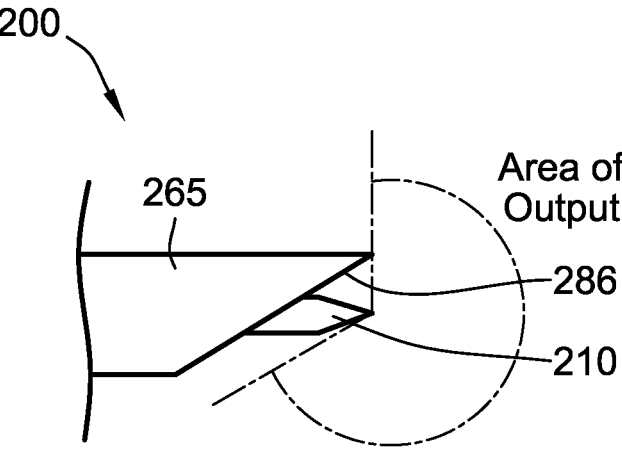
FIG. 10F is an enlarged view of a second alternate embodiment of the illuminated microsurgical instrument with a beveled tip in an open position.

FIG. 10A is an overhead view of an illumination micro-surgical device 200 in accordance with an exemplary embodiment. FIG. 10B is cross-section view of a portion of the illumination microsurgical device 200 showing the surgical tool 250 and optical fiber 210 in accordance with an exemplary embodiment in a closed position. FIG. 10C is an enlarged view of a portion of the illumination microsurgical device 200 showing the surgical tool 250 and optical fiber 210 in accordance with an exemplary embodiment with a non-beveled tip in a closed position. FIG. 10D is an enlarged view of a portion of the illumination microsurgical device 200 showing the surgical tool 250 and optical fiber 210 in accordance with an exemplary embodiment with a non-beveled tip in an open position. FIG. 10E is an enlarged view of a portion of the illumination microsurgical device 200 showing the surgical tool 250 and optical fiber 210 in accordance with an exemplary embodiment with a beveled tip in a closed position. FIG. 10F is an enlarged view of a portion of the illumination microsurgical device 200 showing the surgical tool 250 and optical fiber 210 in accordance with an exemplary embodiment with a beveled tip in an open position.

In the illustrated embodiment shown in FIGS. 10A-10F, the surgical tool 250 is an adjustable light pipe. The adjustable light pipe combines the advantages of a widefield as well as a focal light pipe. The small diameter of the optical fiber 210 and the high intensity and brightness of the light beam emitted from the optical fiber 210 make the surgical tool efficient for surgical procedures. The adjustable light pipe is small enough to not need any suturing when removing from the eye.

The surgical tool 250 includes the tool body 252 extending between the inner end 254 and the outer end 256. The surgical tool 250 includes the handle 258 at the outer end 256 configured to be held by the physician to load the operating portion 260 at the inner end 254 into the eye. For example, the probe 262 is provided at the inner end 254 for insertion into the eye. In an exemplary embodiment, the optical fiber 210 is fixed in place relative to the handle 258 via a fiber couple 284 and a set screw 285 in the handle 258.

In the illustrated embodiment, the surgical tool 250 includes a light pipe tube 265 at the inner end 254. The optical fiber 210 passes through the cavity in the light pipe tube 265. The light pipe tube 265 extends from the front end of the hub 253 of the tool body 252. In an exemplary embodiment, the surgical tool 250 includes a button 257 attached to the light pipe tube 265. The button 257 is able to be actuated (for example, slide relative to the handle 258), which in turn actuates the light pipe tube 265 in position with respect to the tip of the optical fiber 210. The button 257 is actuated forward to the "closed position". In the closed position, the optical fiber 210 is covered or recessed in the light pipe tube 265. The button 257 is actuated rearward to the "open position". In the open position, the tip of the optical fiber 210 protrudes from the front of the light pipe tube 265. In the open position, the light pipe is comparable to a widefield light pipe. The output of the optical fiber 210 can be compared to a room light or a "chandelier." In the closed position, the light pipe is comparable to a focal light pipe. The output of the optical fiber 210 can be compared to a flashlight with a focused/narrow beam of light. The focal beam is more "narrow" compared to a regular focal light pipe. That is, the beam of light is more focused and facilitates use across the eye whereas a normal focal light pipe is unable to do this.

In an exemplary embodiment, the button 257 is able to be actuated continuously from the "open" position to the "closed" position to allow the surgeon to decide how wide the output of light needs to be during use rather than being restricted to a single angle of output. The optical fiber 210 is fixed to the back of the fiber couple 284, the fiber couple 284 is vented to facilitate venting of air when being inserted into the eye. This combats air bubbles being released into the eye during surgery which obstructs the view of the surgeon. The end of the light pipe tube 265 can be provided with a beveled tip to form a shield 286. The shield 286 is positioned between the surgeon and the inside of the eye, which cuts down on glare when being used.

Figure 11A:
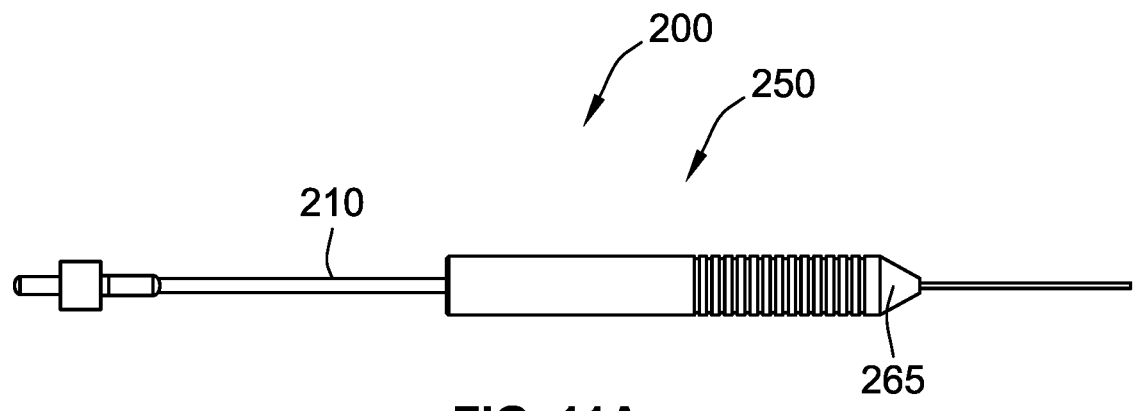
FIG. 11A is an overhead view of a third alternate embodiment of the illuminated microsurgical instrument.
Figure 11B:
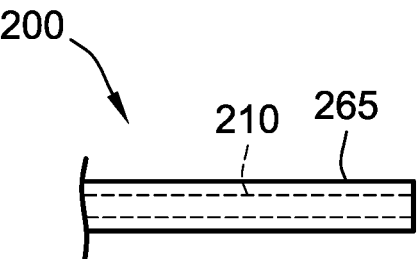
FIG. 11B is an enlarged view of a third alternate embodiment of the illuminated microsurgical instrument with a focal tip.
Figure 11C:
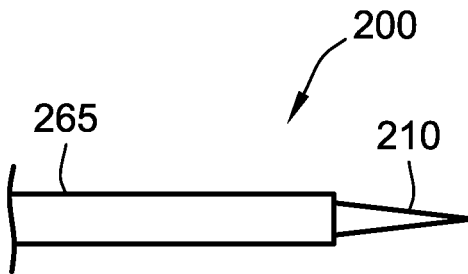
FIG. 11C is an enlarged view of a third alternate embodiment of the illuminated microsurgical instrument with a standard widefield tip.
Figure 11D:
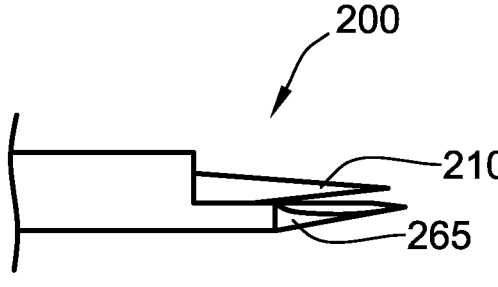
FIG. 11D is an enlarged view of a third alternate embodiment of the illuminated microsurgical instrument with a shielded widefield tip.

FIG. 11A is an overhead view of an illumination microsurgical device 200 in accordance with an exemplary embodiment. FIG. 11B is an enlarged view of a portion of the illumination microsurgical device 200 showing the surgical tool 250 and optical fiber 210 in accordance with an exemplary embodiment with a focal tip. FIG. 11C is an enlarged view of a portion of the illumination microsurgical device 200 showing the surgical tool 250 and optical fiber 210 in accordance with an exemplary embodiment with a widefield tip. FIG. 11D is an enlarged view of a portion of the illumination microsurgical device 200 showing the surgical tool 250 and optical fiber 210 in accordance with an exemplary embodiment with a shielded widefield tip.

In the illustrated embodiment shown in FIGS. 11A-11D, the surgical tool 250 is a light pipe. The small gauge optical fiber 210 forms a small gauge light pipe. The optical fiber 210 is held in the light pipe tube 265. In various embodiments, the optical fibers 210 may have gauge sizes less than 25 ga, such as 29 ga, 30 ga, 31 ga, 32 ga. The tips of the optical fiber 210 can be shaped to produce focal or widefield outputs. Focal outputs are produced by polishing the face of the output side of the fiber flat. Widefield outputs are produced by shaping the tip of the output surface of the fiber into the shape of a cone. Widefield light pipes can be provided with a beveled tip to act as a shield and block glare from obstructing the surgeon's view. Optionally, stiffening sleeves can be provided with the probes to increase probe stiffness.

Figures 12A, 12B, 12C, 12D:
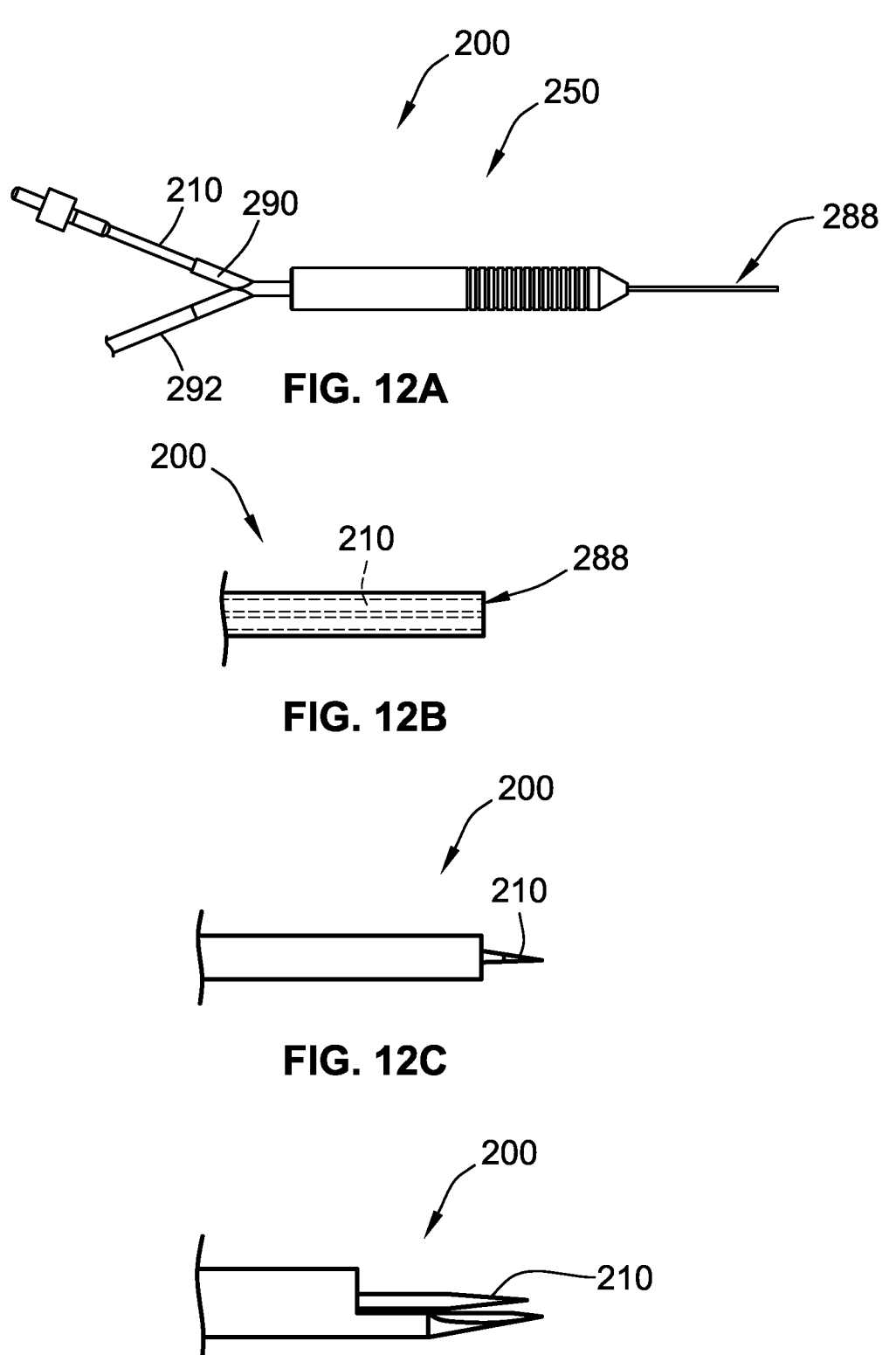
FIG. 12A is an overhead view of a fourth alternate embodiment of the illuminated microsurgical instrument.
FIG. 12B is an enlarged view of a fourth alternate embodiment of the illuminated microsurgical instrument with a focal tip.
FIG. 12C is an enlarged view of a fourth alternate embodiment of the illuminated microsurgical instrument with a standard widefield tip.
FIG. 12D is an enlarged view of a fourth alternate embodiment of the illuminated microsurgical instrument with a shielded widefield tip.

FIG. 12A is an overhead view of an illumination microsurgical device 200 in accordance with an exemplary embodiment. FIG. 12B is an enlarged view of a portion of the illumination microsurgical device 200 showing the surgical tool 250 and optical fiber 210 in accordance with an exemplary embodiment with a focal tip. FIG. 12C is an enlarged view of a portion of the illumination microsurgical device 200 showing the surgical tool 250 and optical fiber 210 in accordance with an exemplary embodiment with a standard widefield tip. FIG. 12D is an enlarged view of a portion of the illumination microsurgical device 200 showing the surgical tool 250 and optical fiber 210 in accordance with an exemplary embodiment with a shielded widefield tip.

In the illustrated embodiment shown in FIGS. 12A-12D, the surgical tool 250 is an aspirating light pipe. The surgical tool 250 allows the combination of a light pipe with the ability to aspirate ILM and ERM from the tips of forceps during bimanual surgery. The surgical tool 250 has a Y connector 290 on the back side that acts the same way as the luer on an MVP. The Y connector 290 allows for the ability to combine the optical fiber 210 with a silicone aspiration line 292. The optical fiber 210 is small enough (50-75 micron) to not obstruct the lumen 288 of the surgical tool 250, therefore keeping the lumen of the surgical tool 250 clear for better aspiration of ILM and ERM. The optical fiber 210 can be provided in a widefield or focal output. The tip of the surgical tool 250 can be beveled to act as a shield to block glare.

Figures 13A, 13B, 13C, 13D:
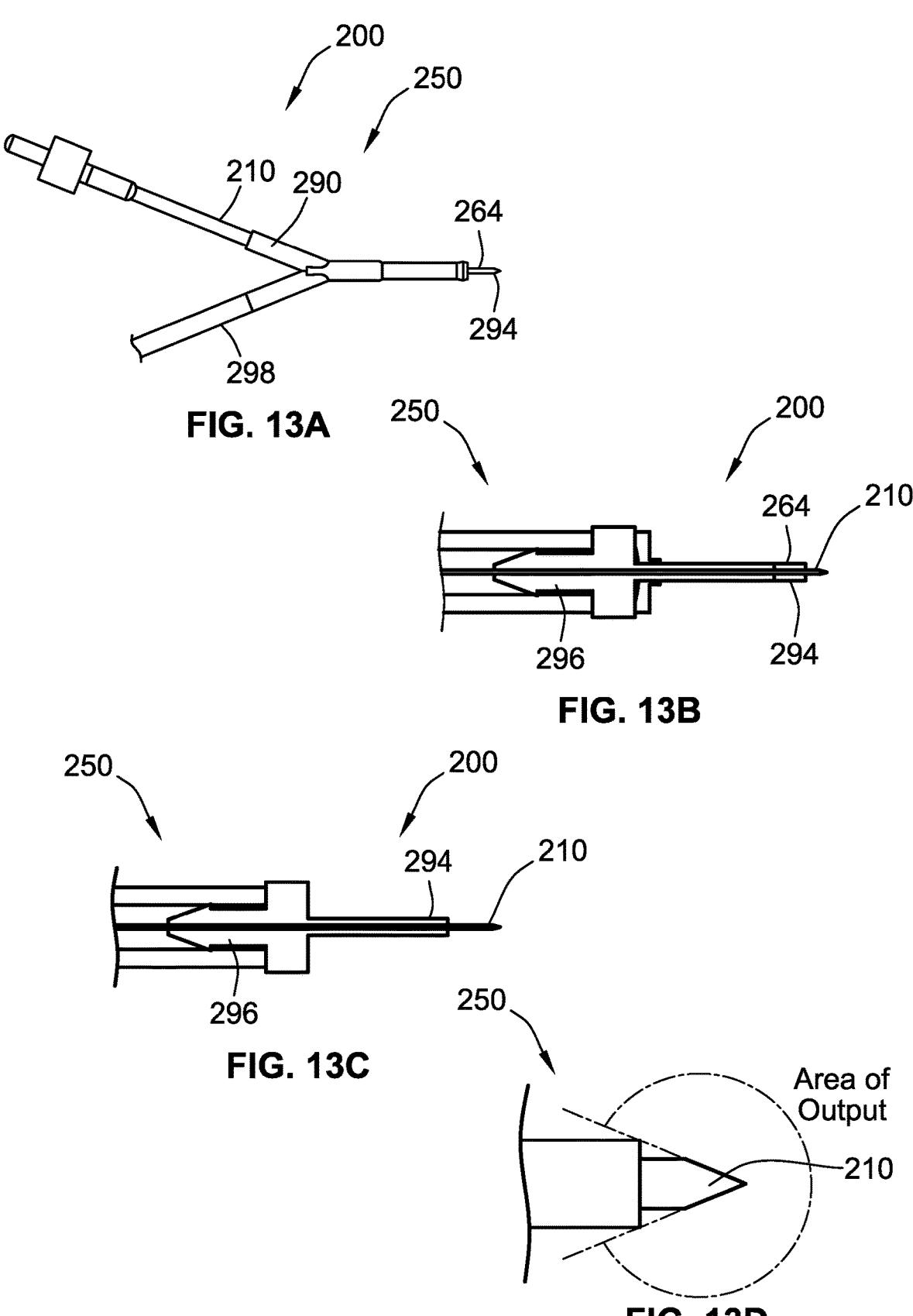
FIG. 13A is an overhead view of a fifth alternate embodiment of the illuminated microsurgical instrument.
FIG. 13B is an enlarged cross-section view of a fifth alternate embodiment of the illuminated microsurgical instrument.
FIG. 13C is another enlarged cross-section view of a fifth alternate embodiment of the illuminated microsurgical instrument with a standard widefield tip.
FIG. 13D is an enlarged view of a fifth alternate embodiment of the illuminated microsurgical instrument illustrating an area of light output.

FIG. 13A is an overhead view of an illumination microsurgical device 200 in accordance with an exemplary embodiment. FIG. 13B is an enlarged cross-section view of a portion of the illumination microsurgical device 200 showing the surgical tool 250 and optical fiber 210 in accordance with an exemplary embodiment. FIG. 13C is another enlarged cross-section view of a portion of the illumination microsurgical device 200 showing the surgical tool 250 and optical fiber 210 in accordance with an exemplary embodiment with a standard widefield tip. FIG. 13D is an enlarged view of a portion of the illumination microsurgical device 200 showing the surgical tool 250 and optical fiber 210 in accordance with an exemplary embodiment illustrating an area of light output.

In the illustrated embodiment shown in FIGS. 13A-13D, the surgical tool 250 is an irrigating chandelier. The surgical tool 250 combines a light pipe, such as a chandelier, with an infusion cannula 294. The light pipe provides efficient illumination due to the brightness provided by the laser diodes and focused light beam. The small gauge of the optical fiber allows adequate infusion rates. For example, the small optical fiber 210 is small enough to provide adequate infusion rates as well as adequate illumination output to be useful during surgery. The small fiber format allows for a smaller overall gauge size while still providing adequate flow rate into the eye. The surgical tool 250 consists of an entry site cannula for the optical fiber 210 as well as the irrigation cannula 294. The irrigation cannula 294 has a luer barb 296 on the backside to connect to the silicone infusion line 298 as well as a tapered needle 264 on the front to provide a secure connection to the entry site cannula. The silicone infusion line 298 is connected to the "Y" connector 290, which combines the optical fiber 210 and the separate infusion line 298. The optical fiber 210 is fed through the Y connector 290 and then into the infusion cannula. The optical fiber 210 is positioned in the Y connector 290 such that it protrudes from the tip of the entry site cannula 294. The entry site cannula 294 can be beveled on the end to provide a "shield" and block glare during the surgery.

Figure 14:
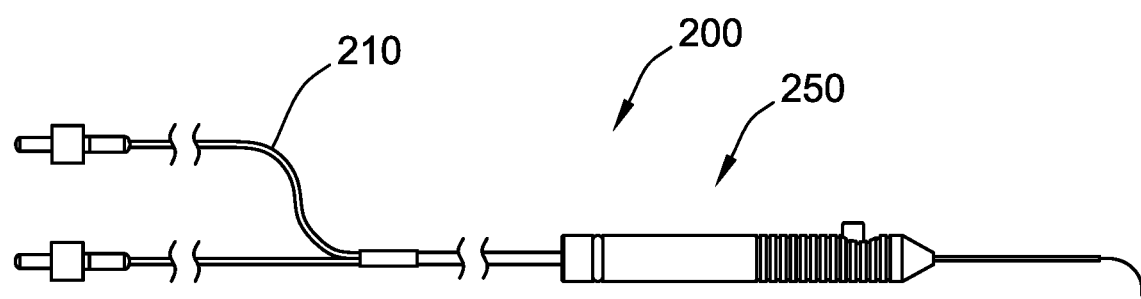
FIG. 14 is an overhead view of a sixth alternate embodiment of the illuminated microsurgical instrument.

FIG. 14 is an overhead view of an illumination microsurgical device 200 in accordance with an exemplary embodiment. In the illustrated embodiment shown in FIG. 14, the surgical tool 250 is a stiff illuminated multi-flex. The Stiff Illuminated Multi-Flex has a small gauge size (such as 27 ga or 29 ga). The small optical fibers 210 used for illumination (50 or 75 micron) facilitates the ability to make the probe in a smaller gauge. A stiffening sleeve may be provided to increase probe stiffness.

Figure 15A:
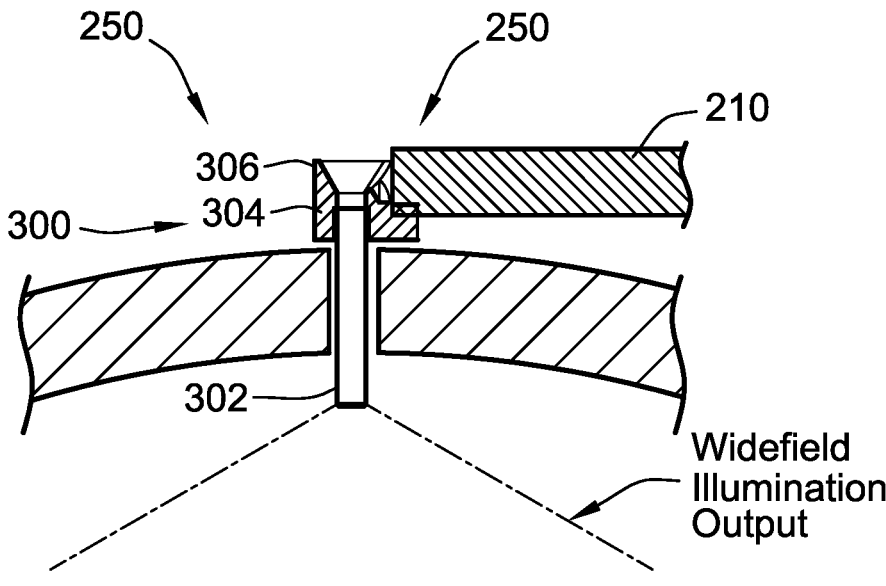
FIG. 15A is a cross-section view of a seventh alternate embodiment of the illuminated microsurgical instrument.
Figure 15B:
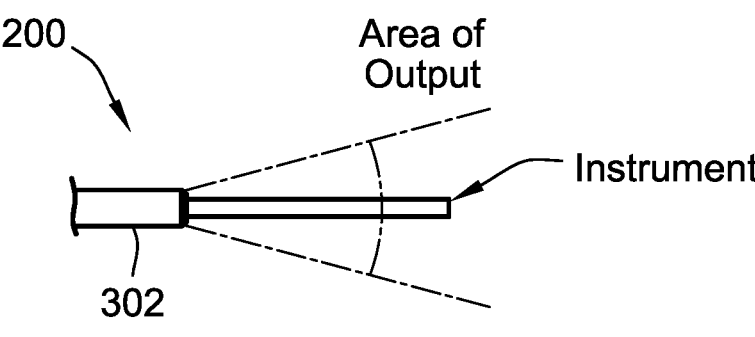
FIG. 15B is an enlarged view of a seventh alternate embodiment of the illuminated microsurgical instrument illustrating a standard area of light output.
Figure 15C:
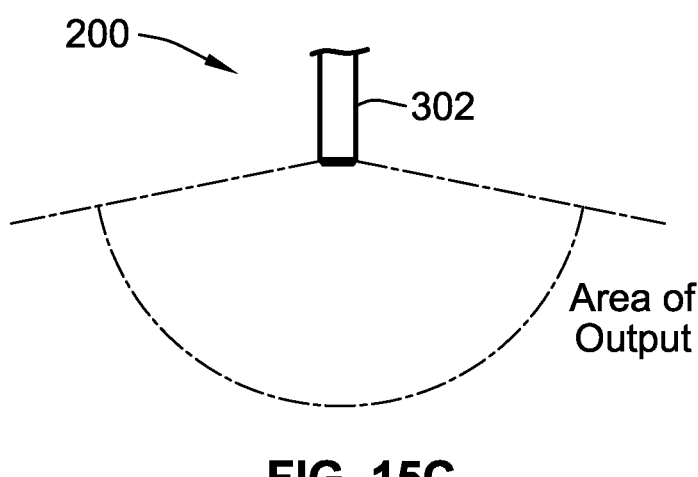
FIG. 15C is an enlarged view of view of a seventh alternate embodiment of the illuminated microsurgical instrument with a wide area of light output.

FIG. 15A is an cross-section view of an illumination microsurgical device 200 in accordance with an exemplary embodiment. FIG. 15B is an enlarged view of a portion of the illumination microsurgical device 200 showing the surgical tool 250 and optical fiber 210 in accordance with an exemplary embodiment illustrating a standard area of light output. FIG. 15C is an enlarged view of view of a portion of the illumination microsurgical device 200 showing the surgical tool 250 and optical fiber 210 in accordance with an exemplary embodiment with a wide area of light output.

In the illustrated embodiment shown in FIGS. 15A-15C, the surgical tool 250 is an illuminated cannula. The illuminated cannula combines an entry site cannula 300 with a chandelier or focal light pipe. The cannula 300 consists of a cannula head 302 and a cannula tube 304. The cannula head 302 and the cannula tube 302 are made of material that is able to accept and transmit light, such as acrylic, borosilicate glass, and the like. The optical fiber 210 has a small diameter (for example, 50-75 micron). The optical fiber 210 is attached to the cannula tube 304 and a jacket 306 secures the optical fiber 210 to the cannula head 302. The tip of the cannula tube 302 can be manufactured to produces a "wide-field" output or a narrow "focal" output. The cannula 300 is desired to be sized in 23 and 25 ga sizes. When used, the interface between the optical fiber 210 and the cannula tube 304 leaks light in a way that illuminates the cannula head 302, removing the need to turn on a room light in order to reinsert an instrument into the eye. When used, the light output will follow the surgical tool 250.

Figure 16A:
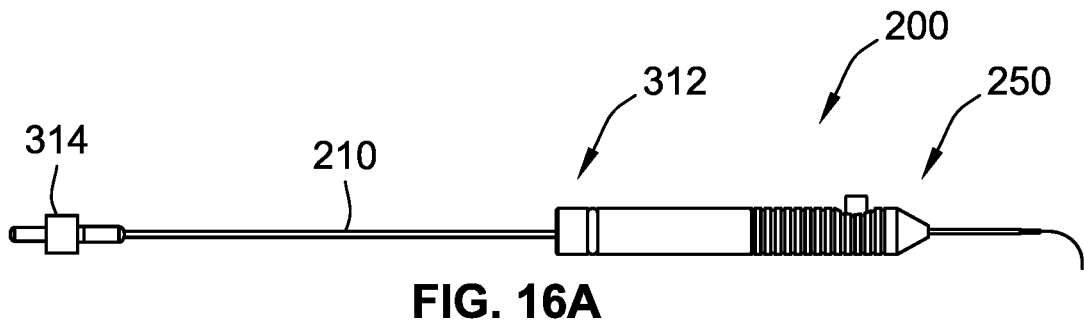
FIG. 16A is an overhead view of an eighth alternate embodiment of the illuminated microsurgical instrument.
Figure 16B:
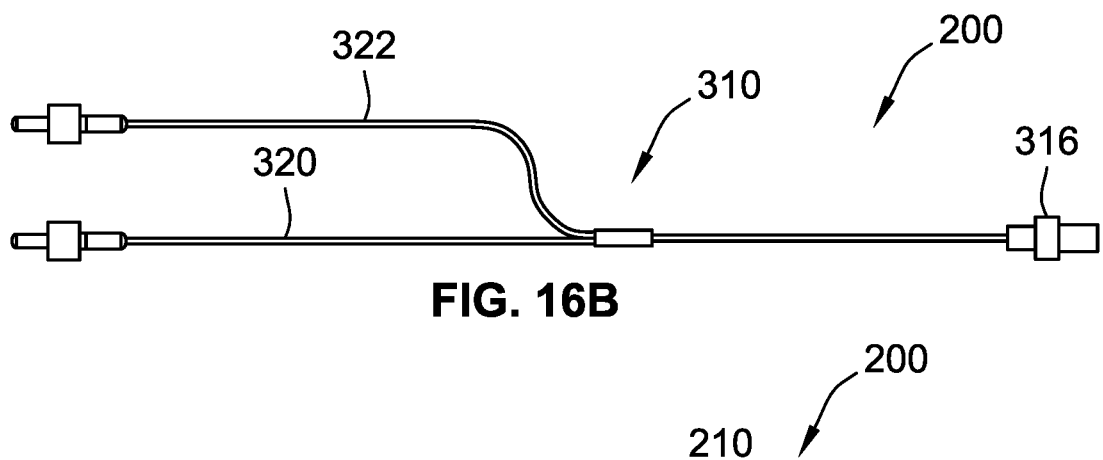
FIG. 16B is an overhead view of a patch cable for the eighth embodiment of the illuminated microsurgical instrument.
Figure 16C:
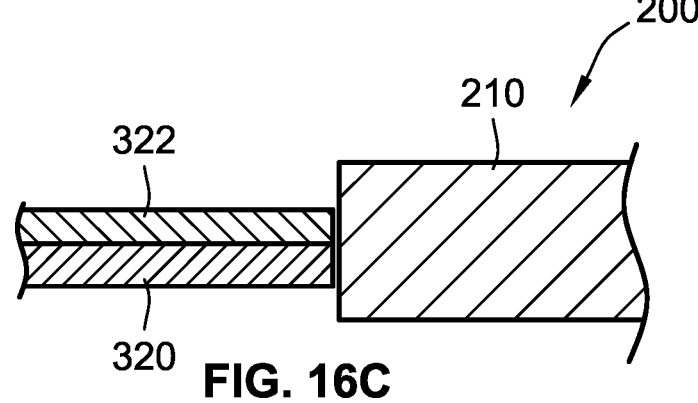
FIG. 16C is an enlarged cross-section view of the patch cable for the eighth embodiment of the illuminated microsurgical instrument.
Figure 16D:
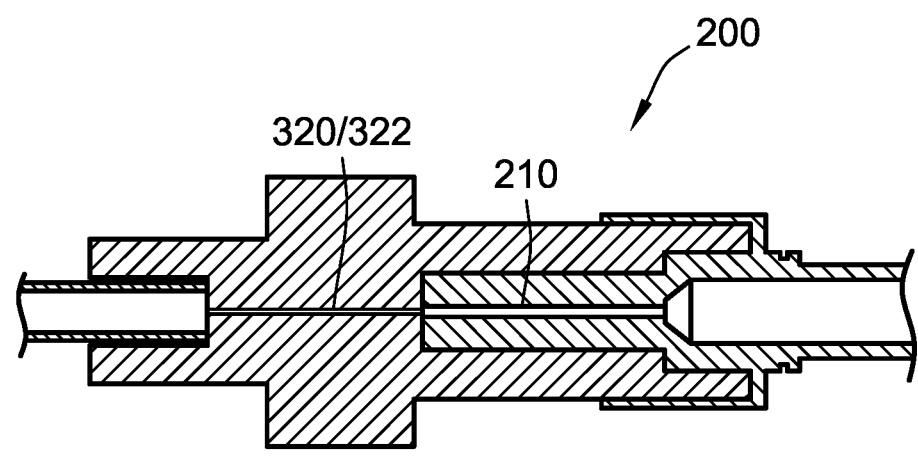
FIG. 16D is an enlarged cross-section view of the eighth embodiment of the illuminated microsurgical instrument.

FIG. 16A is an overhead view of an illumination microsurgical device 200 in accordance with an exemplary embodiment. FIG. 16B is an overhead view of a portion of the illumination microsurgical device 200 showing a patch cable 310 of the surgical tool 250 in accordance with an exemplary embodiment. FIG. 16C is an enlarged cross-section view of the patch cable. FIG. 16D is an enlarged cross-section view of a portion of the illumination microsurgical device 200 showing the surgical tool 250 and optical fiber 210 in accordance with an exemplary embodiment. In the illustrated embodiment shown in FIGS. 16A-16F, the surgical tool 250 is a single fiber stiff illuminated multi-flex. The surgical tool 250 includes the disposable probe 312 and the patch cable 310.

The disposable probe 312 includes a non-illuminated stiff multi-flex laser probe with the optical fiber 210 sized to facilitate the acceptance of two separate spots. The diameter of the optical fiber 210 matches the diameter of the illumination fiber in the patch cable 310. The gauge size of the probe 312 may be a small gauge, such as 27 ga or 29 ga. A stiffening sleeve may be provided to increase probe stiffness. A connector 314 of the probe 312 mates to a receptacle 316 of the patch cable 310.

The patch cable 310 includes a reusable device that consists of a laser fiber 320 and an illumination fiber 322. The two fibers 320, 322 connect to their respective sources and then are run into the receptacle 316. The fibers 320, 322 are polished flat in the receptacle 316. The receptacle 316 accepts the connector 314 that is on the disposable probe 312. The combination of the diameters of the fibers 320, 322 are such that the sum is smaller than the diameter of the single fiber in the disposable probe 312. The illumination fiber diameter is equal to the diameter of the single fiber in the disposable probe 312. The diameter of the laser fiber is smaller than the diameter of the single fiber in the disposable probe 312. The output of each fiber 320, 322 is accepted into the single fiber in the disposable probe 312 and then transmitted into the eye via the single fiber.

Figure 17A:
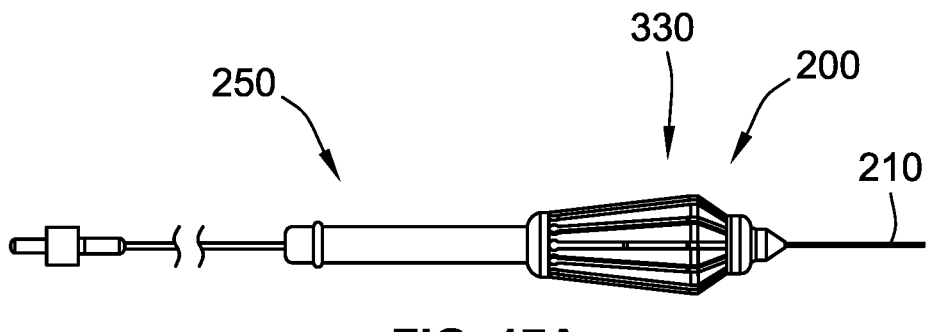
FIG. 17A is a cross-section view of a ninth alternate embodiment of the illuminated microsurgical instrument.
Figure 17B:
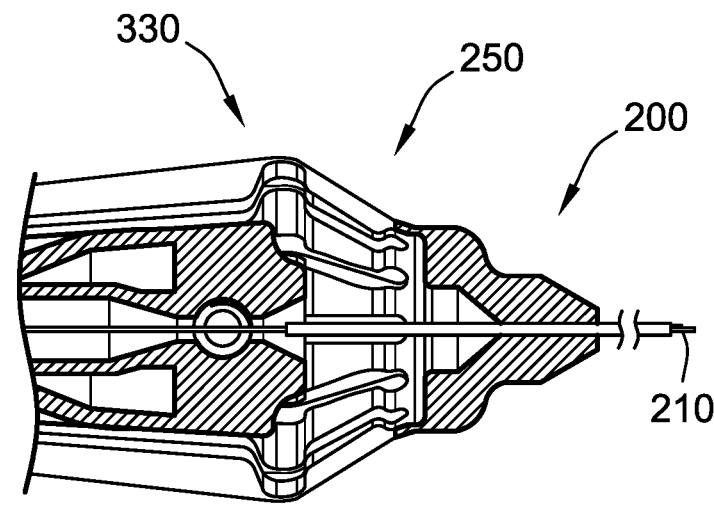
FIG. 17B is an enlarged cross-section view of a ninth alternate embodiment of the illuminated microsurgical instrument.
Figures 17C, 17D:
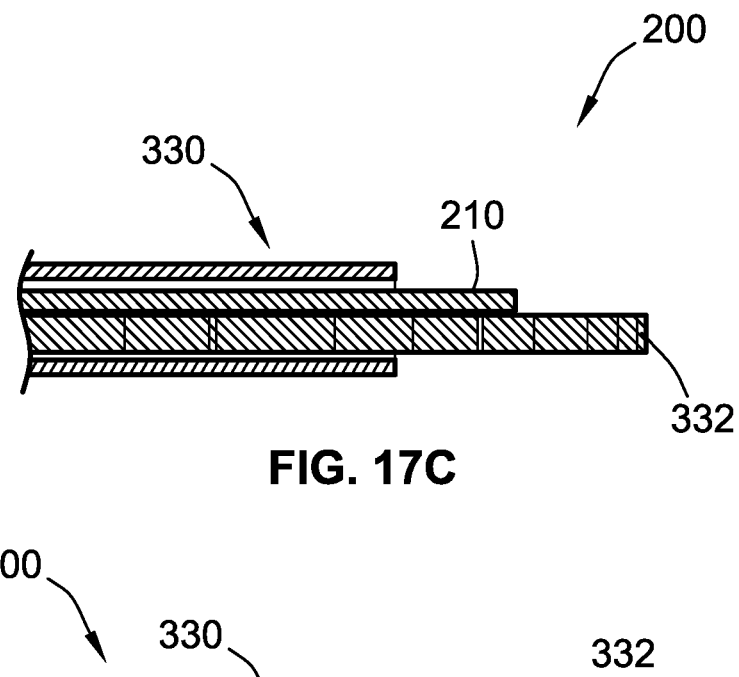
FIG. 17C is an enlarged cross-section view of a ninth alternate embodiment of the illuminated microsurgical instrument with a forceps in the closed position.
FIG. 17D is an cross-section view of a ninth alternate embodiment of the illuminated microsurgical instrument with a forceps in an open position.

FIG. 17A is a cross-section view of an illumination microsurgical device 200 in accordance with an exemplary embodiment. FIG. 17B is an enlarged cross-section view of a portion of the illumination microsurgical device 200 showing the surgical tool 250 and optical fiber 210 in accordance with an exemplary embodiment. FIG. 17C is an enlarged cross-section view of a portion of the illumination microsurgical device 200 showing the surgical tool 250 and optical fiber 210 in accordance with an exemplary embodiment with a forceps in the closed position. FIG. 17D is an cross-section view of a portion of the illumination microsurgical device 200 showing the surgical tool 250 and optical fiber 210 in accordance with an exemplary embodiment with a forceps in an open position.

In the illustrated embodiment shown in FIGS. 17A-17F, the surgical tool 250 is an illuminated forceps. A forceps assembly 330 with the addition of the optical fiber 210 at a tip 332 of the instrument improves the visibility of the surgical field during membrane peeling. The tips 332 may be metal tips. The small fiber format allows for the instrument gauge size to be relatively small, such as 23 ga, 25 ga, 27 ga. The optical fiber 210 is positioned to run through a lumen of the tube next to the welded forceps. However, the optical fiber 210 may be located at other locations, such as in a side by side tubing where one tube houses the forceps, and one tube houses the fiber running the fiber within a partial thickness channel along the length of the tube that houses the forceps. Changing the welded forceps assembly to use a tube instead of a wire, and then putting a hole through the center of the forceps, to allow the fiber to go directly through the welded tubing/forceps assembly and come out in between the forceps tines. The tip of the fiber can be shaped to provide focal or widefield outputs. The forceps/scissors tip style can be many embodiments.

In some example embodiments, a surgical illumination system is provided including a light source having at least one laser diode configured to emit a light beam having a focal point at a focal point plane and an illumination microsurgical device removably coupled to the light source. The illumination microsurgical device includes an optical fiber with a proximal portion configured to receive the light beam from the light source and a distal portion configured to emit the light beam from the light source. The proximal portion has an aperture opening. The size of the focal point is less than the size of the aperture opening.

Optionally, the optical fiber is disposable. Optionally, the illumination microsurgical device includes a device connector at the distal portion that is removably coupled to the light source.

In some aspects, the light source includes a source connector configured to receive the illumination microsurgical device and optically couple the optical fiber to the at least one laser diode. Optionally, the light source includes a bridge optical fiber between the at least one laser diode and the illumination microsurgical device. The bridge optical fiber receives the light beam from the at least one laser diode and transmits the light beam to the optical fiber of the illumination microsurgical device. The bridge optical fiber may have a diameter equal to a diameter of the optical fiber.

In some aspects, the light source may include a light source housing holding the at least laser diode and a control panel having at least one user input for controlling the at least one laser diode. Optionally, the at least one laser diode may include a red laser diode, a blue laser diode, and a green laser diode, wherein the red laser diode configured to emit a red light beam in the red spectral range to the focal point, the blue laser diode configured to emit a blue light beam in the blue spectral range to the focal point, the green laser diode configured to emit a green light beam in the green spectral range to the focal point. The light source may include a beam combiner configured to combine the red light beam, the blude light beam and the green light beam into the light beam and direct the light beam to the focal point. The red laser diode, the blue laser diode, and the green laser diode may be independently controlled to change a color of the light beam.

Optionally, the illumination microsurgical device may include a surgical tool and the distal end of the optical fiber may be integrated into the surgical tool. The illumination microsurgical device may include a cannula having a hollow interior and the optical fiber may be routed through the hollow interior. The illumination microsurgical device may include a probe configured to be inserted into the patient to position the distal portion of the optical fiber relative to the patient. Optionally, the probe includes a cannula at a distal end of the probe having an outer diameter of at most 250 microns and an inner diameter less than the outer diameter. The optical fiber passes through the cannula. The distal portion of the optical fiber may be movable relative to a distal end of the probe to change an output angle of the light beam emitted from the illumination microsurgical device. Optionally, the distal portion of the optical fiber is located interior of the probe to provide a narrow output angle of the light beam and the distal portion of the optical fiber may be located beyond the distal end of the probe to provide a wide output angle of the light beam. Optionally, a distal end of the probe may be beveled to form a shield to block the light beam in one direction more than another direction.

Optionally, an optical spacing may be provided between the focal point plane and the aperture opening. A bridge assembly having a bridge optical fiber may be located in the optical space to connect the optical fiber to the light beam at the focal point plane. Optionally, the optical fiber has a diameter of 200 microns or less.

In an aspect, at least two laser diodes are provided wherein each laser diode has a discrete spectral range. Optionally, the laser diode may have a generally blue spectral range that is within a safe region of the aphakic hazard level.

Optionally, the light source may include a vibratory despeckling mechanism.

In some example embodiments, an illumination microsurgical device is provided including an optical fiber having a proximal portion configured to receive a light beam from a laser diode of a light source and a distal portion configured to emit the light beam. The proximal portion includes an aperture opening having a diameter of 200 microns or less. The illumination microsurgical device includes a device connector at the distal portion configured to be removably coupled to the light source. The illumination microsurgical device includes a surgical tool configured to be inserted into the patient. The distal end of the optical fiber is integrated into the surgical tool for insertion of the distal end of the optical fiber into the patient. The optical fiber, the device connector, and the surgical tool are disposable after use.

Optionally, the device connector is configured to be threadably coupled to a source connector of the light source to position the proximal portion of the optical fiber to receive the light beam from the light source.

In an aspect, the surgical tool includes a cannula having a hollow interior with the optical fiber routed through the hollow interior. The surgical tool may include a probe configured to be inserted into the patient to position the distal portion of the optical fiber relative to the patient. The probe may include a cannula at a distal end of the probe having an outer diameter of at most 250 microns and an inner diameter less than the outer diameter. The optical fiber may pass through the cannula. The distal portion of the optical fiber may be movable relative to a distal end of the probe to change an output angle of the light beam emitted from the illumination microsurgical device. Optionally, the distal portion of the optical fiber is located interior of the probe to provide a narrow output angle of the light beam and the distal portion of the optical fiber may be located beyond the distal end of the probe to provide a wide output angle of the light beam. A distal end of the probe may be beveled to form a shield to block the light beam in one direction more than another direction.

In some example embodiments, a method of manufacturing a surgical illumination system is provided including providing a light source having at least one laser diode configured to emit a light beam and coupling an illumination microsurgical device to the light source to receive the light beam. The illumination microsurgical device includes an optical fiber transmitting the light beam from a proximal portion to a distal portion. The proximal portion has an aperture opening. The method includes focusing the light beam at a focal point at a focal point plane. The size of the focal point is less than the size of the aperture opening.

Optionally, the illumination microsurgical device is removable coupled to the light source and disposable after use. In an aspect, the at least one laser diode includes a red laser diode configured to emit a red light beam in the red spectral range, a blue laser diode configured to emit a blue light beam in the blue spectral range, and a green laser diode configured to emit a green light beam in the green spectral range. The focusing of the light beam at the focal point includes focusing the red light beam to the focal point, focusing the blue light beam to the focal point, and focusing the green light beam to the focal point.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A surgical illumination system comprising:
   a light source having at least one light element configured to emit a light beam, the light beam having a focal point at a focal point plane; and
   an illumination microsurgical device removably coupled to the light source, the illumination microsurgical device comprising:

an optical fiber with a proximal portion configured to receive the light beam from the light source and a distal portion configured to emit the light beam from the light source, the proximal portion having an aperture opening, wherein the optical fiber is integrated into the illumination microsurgical device, and wherein the distal portion extends from an end of the illumination microsurgical device;

wherein the size of the focal point is less than the size of the aperture opening;

wherein the light source includes a source connector configured to receive the illumination microsurgical device and optically couple the optical fiber to the at least one light element.

2. The surgical illumination system of claim 1, wherein the illumination microsurgical device comprises a device connector at the proximal portion, the device connector being removably coupled to the light source.

3. The surgical illumination system of claim 1, wherein the light source comprises a bridge optical fiber between the at least one light element and the illumination microsurgical device, the bridge optical fiber receiving the light beam from the at least one light element and transmitting the light beam to the optical fiber of the illumination microsurgical device.

4. The surgical illumination system of claim 3, wherein the bridge optical fiber has a diameter equal to a diameter of the optical fiber.

5. The surgical illumination system of claim 1, wherein the light source comprises a light source housing holding the at least one light element, the light source comprising a control panel having at least one user input for controlling the at least one light element.

6. The surgical illumination system of claim 1, wherein the at least one light element comprises a red laser diode, a blue laser diode, and a green laser diode, the red laser diode configured to emit a red light beam in the red spectral range to the focal point, the blue laser diode configured to emit a blue light beam in the blue spectral range to the focal point, the green laser diode configured to emit a green light beam in the green spectral range to the focal point.

7. The surgical illumination system of claim 6, wherein the light source comprises a beam combiner configured to combine the red light beam, the blue light beam and the green light beam into the light beam and direct the light beam to the focal point.

8. The surgical illumination system of claim 6, wherein the red laser diode, the blue laser diode, and the green laser diode are independently controlled to change a color of the light beam, or to produce white light.

9. The surgical illumination system of claim 1, wherein the illumination microsurgical device comprises a surgical tool, wherein the surgical tool is at least one of a disposable light pipe, a tangential illuminator, an adjustable field output illuminator, an aspirating endoilluminator, a slit output illuminator, a chandelier illuminator, an irrigating chandelier, an illuminated cannula, or an illuminated laser probe.

10. The surgical illumination system of claim 9, wherein the distal portion of the optical fiber is movable relative to a distal end of the surgical tool to change an output angle of the light beam emitted from the illumination microsurgical device.

11. The surgical illumination system of claim 10, wherein the distal portion of the optical fiber is located interior of the surgical tool to provide a narrow output angle of the light beam and wherein the distal portion of the optical fiber is located beyond the distal end of the surgical tool to provide a wide output angle of the light beam.

12. The surgical illumination system of claim 9, wherein a distal end of the surgical tool is beveled to form a shield to block the light beam in one direction more than another direction.

13. The surgical illumination system of claim 1, wherein the optical fiber has a diameter of 200 microns or less.

14. The surgical illumination system of claim 1, further comprising at least two light elements wherein each light element has a discrete spectral range.

15. The surgical illumination system of claim 1, wherein the light source comprises a despeckling mechanism.

* * * * *